United States Patent [19]

Hardman et al.

[11] Patent Number: 5,866,124
[45] Date of Patent: Feb. 2, 1999

[54] ANTIIDIOTYPIC ANTIBODIES FOR HIGH MOLECULAR WEIGHT-MELANOMA ASSOCIATED ANTIGEN

[75] Inventors: Norman Hardman, Riehen, Switzerland; Gerd Pluschke, Merzhausen, Germany; Brendan Murray, Nelkenring, Switzerland

[73] Assignee: Novartis Corporation, Summit, N.J.

[21] Appl. No.: 650,262

[22] PCT Filed: Mar. 5, 1993

[86] PCT No.: PCT/EP93/00505

§ 371 Date: Sep. 14, 1994

§ 102(e) Date: Sep. 14, 1994

[87] PCT Pub. No.: WO93/19180

PCT Pub. Date: Sep. 30, 1993

Related U.S. Application Data

[63] Continuation of Ser. No. 302,824, Sep. 14, 1994, abandoned.

[30] Foreign Application Priority Data

Mar. 17, 1992 [DE] Germany ........................... 92810188.0

[51] Int. Cl.⁶ .................. A61K 39/395; C07K 16/42; C12P 21/08; G01N 33/574
[52] U.S. Cl. ..................... 424/131.1; 424/133.1; 435/810; 435/7.23; 530/387.2; 530/387.3
[58] Field of Search .............................. 530/387.1, 387.2, 530/387.3; 536/23.53; 435/70.1, 7.1, 320.1, 327, 328, 810, 7.23; 424/9.1, 131.1, 133.1

[56] References Cited

U.S. PATENT DOCUMENTS 4,918,164  4/1990  Hellstrom et al. .

FOREIGN PATENT DOCUMENTS

| 0428485 | 11/1990 | European Pat. Off. . |
|---|---|---|
| WO 85/02121 | 5/1985 | WIPO . |
| WO 89/11296 | 11/1989 | WIPO . |
| WO 91/04055 | 4/1991 | WIPO . |

OTHER PUBLICATIONS

Edmundson et al. [*Immunochemistry*, ed. Weir, Blackwell Scientific Publications, Oxford, Chapter 15 (1986)].
Parham et al. [*Immunochemistry*, ed. Weir, Blackwell Scientific Publications, Oxford, Chapter 14 (1986)].
European Search Report, EP 92/810188, Issued Dec. 2, 1992.
Alanen, A., et al., "Sequence and Linkage of the $V_x21A$ and G Germ–line Gene Segments in the Mouse", *Eur. J. Immunol.*, 19:1961–1963 (1989).
Chattopadhyay, P., et al., "Murine Monoclonal Anti–idiotope Antibody Breaks Unresponsiveness and Induces a Specific Antibody Response to Human Melanoma–associated Proteoglycan Antigen in Cynomolgus Monkeys", *PNAS*, 89:2684–2688 (1992).
Giacomini, P., et al., "Analysis of the Interaction Between a Human High Molecular Weight Melanoma–associated Antigen and the Monoclonal Antibodies to Three Distinct Antigenic Dterminants", *J. Immunology*, 135(1):696–702 (1985).
Herlyn, D., et al., "Anti–Idiotypic Antibodies Bear the Internal Image of a Human Tumor Antigen", *Science*, 232:100–102 (1986).
Kusama, M., et al., "Antidiotypic Monoclonal Antibodies to Anti–human High Molecular Weight–melanoma Associated Antigen Monoclonal Antibodies", *Abstract 1429, Proceedings of AACR*, 28:361 (Mar., 1987).
Kusama, M., et al., "Syngereic Antiidiotypic Antisera to Murine Antihuman High–Molecular–Weight Melanoma–associated Antigen Monoclonal Antibodies", *Cancer Research*, 47:4312–4317 (1987).
Kusama, M., et al., "Syngeneic Monoclonal Antiidiotypic Antibodies to Murine Anti–Human High Molecular Weight–Melanoma Associated Antigen Monoclonal Antibodies", in *Monoclonals and DNA Probes in Diagnostic and Preventive Medicine*, Robert C. Gallo et al; eds. Raven Press, New York, 101–110 (1987).
Kusama, M., et al., "Characterization of Syngeneic Antiidiotypic Monoclonal Antibodies to Murine Anti–Human High Molecular Weight Melanoma–Associated Antigen Monoclonal Antibodies", *J. Immunology*, 143:3844–3852 (1989).
Lee, V.K., et al., "Idiotypic Interactions in Immune Responses to Tumor–associated Antigens", *Biochim. Biophys. Acta*, 865:127–139 (1986).
Mittelman, A., et al., "A Phase I Clinical Trial of Murine Anti–idiotypic Monoclonal Antibodies to Anti Human High Molecular Weight—Melanoma Associated Antigen Monoclonal Antibodies in Patients with Malignant Melanoma", *Abstract 1548, Proceedings of AACR*, 28:390 (1987).
Mittelman, A., et al., "Human High Molecular Weight Melanoma–associated Antigen (HMW–MAA) Mimicry by Mouse Anti–idiotypic Monoclonal Antibody MK2–23: Induction of Humoral Anti–HMW–MAA Immunity and Prolongation of Survival in Patients with Stage IV Melanoma", *PNAS*, 89:466–470 (1992).
Riechmann, L., et al., "Reshaping Human Antibodies for Therapy", *Nature*, 332:323–327 (1988).

(List continued on next page.)

Primary Examiner—Christina Chan
Assistant Examiner—F. Pierre VanderVegt
Attorney, Agent, or Firm—Hesna J. Pfeiffer

[57] ABSTRACT

The invention concerns antiidiotypic antibodies comprising human constant regions, and murine variable regions bearing the internal image of human high molecular weight-melanoma associated antigen which have the specificity of said antibody. These antiidiotypic monoclonal antibodies have immune-regulatory functions and can therefore be used for diagnostic and therapeutic purposes, such as the treatment of melanoma.

4 Claims, No Drawings

OTHER PUBLICATIONS

Tsujisaki, M., et al., "A Sandwish Assay to Detect and Characterize Syngeneic Anti–idiotypic Antibodies to Murine Anti–HLA and Tumor Associated Antigen Monoclonal Antibodies", *J. Immun. Methods*, 95:47–55 (1986).

Tsujisake, M., et al., "Syngeneic Polyclonal and Monoclonal Antiidiotypic Antibodies to Murine Anti–Human High Molecular Weight–Melanoma Associated Antigen and Anti–HLA Monoclonal Antibodies", in *Cellular, Molecular and Genetic Approaches to Immunodiagnosis and Immunotherapy*, K. Kano et al., eds., Karger, Basel, 251–258 (1987).

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 334 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 7..330
        ( D ) OTHER INFORMATION: /note= "light chain variable domain of antibody MK 2-CHgamma1"

( i x ) FEATURE:
        ( A ) NAME/KEY: misc_feature
        ( B ) LOCATION: 1..24
        ( D ) OTHER INFORMATION: /function= "primer VK? BACK"

( i x ) FEATURE:
        ( A ) NAME/KEY: misc_feature
        ( B ) LOCATION: 7..12
        ( D ) OTHER INFORMATION: /function=0 "restriction site PVUII"

( i x ) FEATURE:
        ( A ) NAME/KEY: misc_feature
        ( B ) LOCATION: 70..114
        ( D ) OTHER INFORMATION: /function= "CDR1L"

( i x ) FEATURE:
        ( A ) NAME/KEY: misc_feature
        ( B ) LOCATION: 163..180
        ( D ) OTHER INFORMATION: /function= "CDR2L"

( i x ) FEATURE:
        ( A ) NAME/KEY: misc_feature
        ( B ) LOCATION: 277..303
        ( D ) OTHER INFORMATION: /function= "CDR3L"

( i x ) FEATURE:
        ( A ) NAME/KEY: misc_feature
        ( B ) LOCATION: 314..334
        ( D ) OTHER INFORMATION: /function= "cDNA to primer VK1FOR"

( i x ) FEATURE:
        ( A ) NAME/KEY: misc_feature
        ( B ) LOCATION: 326..331
        ( D ) OTHER INFORMATION: /function= "restriction site BGLII"

( x i ) SEQUENCE DESCRIPTION: SEQ ID NO:1:

```
GACATT CAG CTG ACC CAG TCT CCA GCT TCT CTG GCT GTG TCT CTT GGG              48
       Gln Leu Thr Gln Ser Pro Ala Ser Leu Ala Val Ser Leu Gly
        1           5                   10

CAG AGA GTC ACC ATC TCC TGC AGA GCC AGT GAA AGT GTT GAA TAT TAT             96
Gln Arg Val Thr Ile Ser Cys Arg Ala Ser Glu Ser Val Glu Tyr Tyr
 15          20                  25                  30

GGC TCA AGT TTA ATG CAG TGG TAT CAA CAG AAA CCA GGA CAG CCA CCC            144
```

```
Gly  Ser  Ser  Leu  Met  Gln  Trp  Tyr  Gln  Gln  Lys  Pro  Gly  Gln  Pro  Pro
               35                       40                       45

AAA  CTC  CTC  ATC  TAT  GCT  GCA  TCC  AAC  GTA  GAA  TCT  GGG  GTC  CCT  GCC    192
Lys  Leu  Leu  Ile  Tyr  Ala  Ala  Ser  Asn  Val  Glu  Ser  Gly  Val  Pro  Ala
               50                       55                       60

AGG  TTT  AGT  GGC  AGT  GGG  TCT  GGG  ACA  GAC  TTC  AGC  CTC  AAC  ATC  CAT    240
Arg  Phe  Ser  Gly  Ser  Gly  Ser  Gly  Thr  Asp  Phe  Ser  Leu  Asn  Ile  His
               65                       70                       75

CCT  GTG  GAG  GAG  GAT  GAT  ATT  GCA  ATG  TAT  TTC  TGT  CAG  CAA  AGT  AGG    288
Pro  Val  Glu  Glu  Asp  Asp  Ile  Ala  Met  Tyr  Phe  Cys  Gln  Gln  Ser  Arg
          80                       85                       90

AAA  ATT  CCG  TAC  ACG  TTC  GGA  GGG  GGG  ACC  AAG  CTG  GAG  ATC              330
Lys  Ile  Pro  Tyr  Thr  Phe  Gly  Gly  Gly  Thr  Lys  Leu  Glu  Ile
 95                      100                     105

TAAC                                                                               334
```

( 2 ) INFORMATION FOR SEQ ID NO:2:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Gln  Leu  Thr  Gln  Ser  Pro  Ala  Ser  Leu  Ala  Val  Ser  Leu  Gly  Gln  Arg
 1                   5                    10                       15

Val  Thr  Ile  Ser  Cys  Arg  Ala  Ser  Glu  Ser  Val  Glu  Tyr  Tyr  Gly  Ser
               20                       25                       30

Ser  Leu  Met  Gln  Trp  Tyr  Gln  Gln  Lys  Pro  Gly  Gln  Pro  Pro  Lys  Leu
               35                       40                       45

Leu  Ile  Tyr  Ala  Ala  Ser  Asn  Val  Glu  Ser  Gly  Val  Pro  Ala  Arg  Phe
          50                       55                       60

Ser  Gly  Ser  Gly  Ser  Gly  Thr  Asp  Phe  Ser  Leu  Asn  Ile  His  Pro  Val
 65                      70                       75                       80

Glu  Glu  Asp  Asp  Ile  Ala  Met  Tyr  Phe  Cys  Gln  Gln  Ser  Arg  Lys  Ile
               85                       90                       95

Pro  Tyr  Thr  Phe  Gly  Gly  Gly  Thr  Lys  Leu  Glu  Ile
               100                      105
```

( 2 ) INFORMATION FOR SEQ ID NO:3:

( i ) SEQUENCE CHARACTERISTICS:
        ( A ) LENGTH: 368 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 9..359
        ( D ) OTHER INFORMATION: /note= "heavy chain variable domain
                of antibody MK2-CHgamma1"

( i x ) FEATURE:
        ( A ) NAME/KEY: misc_feature
        ( B ) LOCATION: 1..22
        ( D ) OTHER INFORMATION: /phenotype= "prmier VH1BACK"

( i x ) FEATURE:
        ( A ) NAME/KEY: misc_feature (B) LOCATION: 1..14
(D) OTHER INFORMATION: /function= "restriction site PSTI"

(ix) FEATURE:
(A) NAME/KEY: misc_feature
(B) LOCATION: 90..104
(D) OTHER INFORMATION: /function= "CDR1H"

(ix) FEATURE:
(A) NAME/KEY: misc_feature
(B) LOCATION: 147..197
(D) OTHER INFORMATION: /function= "CDR2H"

(ix) FEATURE:
(A) NAME/KEY: misc_feature
(B) LOCATION: 294..335
(D) OTHER INFORMATION: /function= "CDR3H"

(ix) FEATURE:
(A) NAME/KEY: misc_feature
(B) LOCATION: 335..368
(D) OTHER INFORMATION: /function= "cDNA to primer VH1FOR"

(ix) FEATURE:
(A) NAME/KEY: misc_feature
(B) LOCATION: 353..359
(D) OTHER INFORMATION: /function= "restriction site BstEII"

(xi) SEQUENCE DESCRIPTION: SEQ ID NO:3:

```
AGGTGCAG CTG CAG GAG TCT GGG GGA GGC TTA GTG CAG CCT GGA GGG TCC        50
         Leu Gln Glu Ser Gly Gly Gly Leu Val Gln Pro Gly Gly Ser
         110                     115                 120

CGG AAA CTC TCC TGT GCA GCC TCT GGA TTC ACT TTC AGT AGC TTT GGA         98
Arg Lys Leu Ser Cys Ala Ala Ser Gly Phe Thr Phe Ser Ser Phe Gly
        125                 130                 135

ATG CAC TGG GTT CGT CAG GCT CCA GAG AAG GGG CTG GAG TGG GTC GCA        146
Met His Trp Val Arg Gln Ala Pro Glu Lys Gly Leu Glu Trp Val Ala
140                     145                 150

TAC ATT AGT AGT GAC AGT AGT AAC ATC TAC TAT GCA GAC ACA GTG AAG        194
Tyr Ile Ser Ser Asp Ser Ser Asn Ile Tyr Tyr Ala Asp Thr Val Lys
155                 160                 165                 170

GGC CGA TTC ACC ATC TCC AGA GAC AAT CCC AAG AAC ACC CTG TTC CTG        242
Gly Arg Phe Thr Ile Ser Arg Asp Asn Pro Lys Asn Thr Leu Phe Leu
                175                 180                 185

CAA ATG ACC AGT CTA AGG TCT GAG GAC ACG GCC ATG TAT TAC TGT GCA        290
Gln Met Thr Ser Leu Arg Ser Glu Asp Thr Ala Met Tyr Tyr Cys Ala
            190                 195                 200

AGA TCG AAC TAT GTT GGT TAC CAC GTC CGG TGG TAC TTC GAT GTC TGG        338
Arg Ser Asn Tyr Val Gly Tyr His Val Arg Trp Tyr Phe Asp Val Trp
        205                 210                 215

GGC CAA GGG ACC ACG GTC ACC GTCTCCTCA                                  368
Gly Gln Gly Thr Thr Val Thr
220             225
```

(2) INFORMATION FOR SEQ ID NO:4:

(i) SEQUENCE CHARACTERISTICS:
(A) LENGTH: 117 amino acids
(B) TYPE: amino acid
(D) TOPOLOGY: linear (ii) MOLECULE TYPE: protein (xi) SEQUENCE DESCRIPTION: SEQ ID NO:4:

```
Leu Gln Glu Ser Gly Gly Gly Leu Val Gln Pro Gly Gly Ser Arg Lys
1               5                   10                  15

Leu Ser Cys Ala Ala Ser Gly Phe Thr Phe Ser Ser Phe Gly Met His
            20                  25                  30
```

```
Trp Val Arg Gln Ala Pro Glu Lys Gly Leu Glu Trp Val Ala Tyr Ile
        35                  40                  45

Ser Ser Asp Ser Ser Asn Ile Tyr Tyr Ala Asp Thr Val Lys Gly Arg
        50                  55                  60

Phe Thr Ile Ser Arg Asp Asn Pro Lys Asn Thr Leu Phe Leu Gln Met
65                      70                  75                  80

Thr Ser Leu Arg Ser Glu Asp Thr Ala Met Tyr Tyr Cys Ala Arg Ser
                85                  90                  95

Asn Tyr Val Gly Tyr His Val Arg Trp Tyr Phe Asp Val Trp Gly Gln
            100             105                 110

Gly Thr Thr Val Thr
        115
```

( 2 ) INFORMATION FOR SEQ ID NO:5:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide primer VH1FOR"

( i i i ) HYPOTHETICAL: NO ( x i ) SEQUENCE DESCRIPTION: SEQ ID NO:5:

TGAGGAGACG GTGACCGTGG TCCCTTGGCC CCAG     34

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide primer VH1BACK"

( i i i ) HYPOTHETICAL: NO ( x i ) SEQUENCE DESCRIPTION: SEQ ID NO:6:

AGGTSMARCT GCAGSAGTCW GG     22

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide primer VK1FOR"

( i i i ) HYPOTHETICAL: NO ( x i ) SEQUENCE DESCRIPTION: SEQ ID NO:7:

GTTAGATCTC CAGCTTGGTS CS     22

( 2 ) INFORMATION FOR SEQ ID NO:8:

( i ) SEQUENCE CHARACTERISTICS:
        ( A ) LENGTH: 24 base pairs
        ( B ) TYPE: nucleic acid (C) STRANDEDNESS: single
(D) TOPOLOGY: linear (ii) MOLECULE TYPE: other nucleic acid
(A) DESCRIPTION: /desc = "oligonucleotide primer VK1BACK"

(iii) HYPOTHETICAL: NO (xi) SEQUENCE DESCRIPTION: SEQ ID NO:8:

GACATTCAGC TGACCCAGTC TCCA 24

(2) INFORMATION FOR SEQ ID NO:9:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "oligonucleotide primer M/Ckappa"

(iii) HYPOTHETICAL: NO (xi) SEQUENCE DESCRIPTION: SEQ ID NO:9:

GGGAAGATGG ATACAGTTGG 20

(2) INFORMATION FOR SEQ ID NO:10:

(i) SEQUENCE CHARACTERISTICS:
(A) LENGTH: 15 amino acids
(B) TYPE: amino acid
(D) TOPOLOGY: linear (ii) MOLECULE TYPE: peptide (iii) HYPOTHETICAL: NO (xi) SEQUENCE DESCRIPTION: SEQ ID NO:10:

Arg Ala Ser Glu Ser Val Glu Tyr Tyr Gly Ser Ser Leu Met Gln
1               5                   10                  15

(2) INFORMATION FOR SEQ ID NO:11:

(i) SEQUENCE CHARACTERISTICS:
(A) LENGTH: 7 amino acids
(B) TYPE: amino acid
(D) TOPOLOGY: linear (ii) MOLECULE TYPE: peptide (iii) HYPOTHETICAL: NO (xi) SEQUENCE DESCRIPTION: SEQ ID NO:11:

Ala Ala Ser Asn Val Glu Ser
1               5

(2) INFORMATION FOR SEQ ID NO:12:

(i) SEQUENCE CHARACTERISTICS:
(A) LENGTH: 9 amino acids
(B) TYPE: amino acid
(D) TOPOLOGY: linear (ii) MOLECULE TYPE: peptide (iii) HYPOTHETICAL: NO (xi) SEQUENCE DESCRIPTION: SEQ ID NO:12:

```
Gln  Gln  Ser  Arg  Lys  Ile  Pro  Tyr  Thr
1                 5
```

( 2 ) INFORMATION FOR SEQ ID NO:13:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:13:

```
Ser  Phe  Gly  Met  His
1                 5
```

( 2 ) INFORMATION FOR SEQ ID NO:14:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:14:

```
Tyr  Ile  Ser  Ser  Asp  Ser  Ser  Asn  Ile  Tyr  Tyr  Ala  Asp  Thr  Val
1                 5                         10                        15
Lys  Gly
```

( 2 ) INFORMATION FOR SEQ ID NO:15:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:15:

```
Ser  Asn  Tyr  Val  Gly  Tyr  His  Val  Arg  Trp  Tyr  Phe  Asp  Val
1                 5                         10
```

( 2 ) INFORMATION FOR SEQ ID NO:16:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( x i ) SEQUENCE DESCRIPTION: SEQ ID NO:16:

```
GGTGACC                                                                 7
```

( 2 ) INFORMATION FOR SEQ ID NO:17:

( i ) SEQUENCE CHARACTERISTICS:
        ( A ) LENGTH: 6 base pairs
        ( B ) TYPE: nucleic acid
        ( C ) STRANDEDNESS: single (D) TOPOLOGY: linear (i i) MOLECULE TYPE: other nucleic acid (i i i) HYPOTHETICAL: NO (x i) SEQUENCE DESCRIPTION: SEQ ID NO:17:

CTGCAG 6

(2) INFORMATION FOR SEQ ID NO:18:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (i i) MOLECULE TYPE: other nucleic acid (i i i) HYPOTHETICAL: NO (x i) SEQUENCE DESCRIPTION: SEQ ID NO:18:

AGATCT 6

(2) INFORMATION FOR SEQ ID NO:19:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (i i) MOLECULE TYPE: other nucleic acid (i i i) HYPOTHETICAL: NO (x i) SEQUENCE DESCRIPTION: SEQ ID NO:19:

CAGCTG 6

(2) INFORMATION FOR SEQ ID NO:20:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (i i) MOLECULE TYPE: other nucleic acid (i i i) HYPOTHETICAL: NO (x i) SEQUENCE DESCRIPTION: SEQ ID NO:20:

CCCATGGG 8

(2) INFORMATION FOR SEQ ID NO:21:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (i i) MOLECULE TYPE: other nucleic acid (i i i) HYPOTHETICAL: NO (x i) SEQUENCE DESCRIPTION: SEQ ID NO:21:

CTCTAGAG 8

ANTIIDIOTYPIC ANTIBODIES FOR HIGH MOLECULAR WEIGHT-MELANOMA ASSOCIATED ANTIGEN

This application is a continuation, of application Ser. No. 08/302,824, filed Sep. 14, 1994, now abandoned which is a PCT National Stage application of PCT/EP93/00505, filed Mar. 5, 1993.

The invention concerns antiidiotypic monoclonal antibodies comprising human constant regions, and variable regions bearing the internal image of human high molecular weight-melanoma associated antigen (HMW-MAA), and derivatives of said antibodies. The antibodies of the invention and their derivatives are useful for diagnostic, prophylactic and therapeutic purposes, such as the immune therapy of melanoma.

BACKGROUND OF THE INVENTION

Melanomas are tumors of the skin, less frequently of mucous membranes, some of which are benign. Malignant melanomas are carcinomas of neuroectodermal origin generally derived from melanocytes (pigment-producing cells), sometimes from mucous membranes, the chorioid coat or the meninges. There are several types of malignant melanoma which differ in localization, way of spreading and production of metastases.

Conventional treatment of melanoma includes surgery, radio- or chemotherapy, and the application of biological response modifiers. However, these methods have proved to be insufficient to combat the illness, e.g. to prevent tumor recurrence, and are complicated by a large number of severe side effects. Therefore, it is desirable to develop therapeutic approaches which overcome these drawbacks and can replace or be used in combination with conventional treatment.

Since the immune system seems to be heavily involved in the pathogenesis of this disease, the most suitable treatment would be a method of active immunotherapy, for example based on the application of specific antiidiotypic antibodies. Of special interest for therapeutic application are antiidiotypic antibodies of the internal image type which mimic the initial antigen and can substitute for it.

For tumor therapy, suitable antiidiotypic antibodies are those which are raised against antibodies specific for tumor associated antigens. In melanoma, one of the associated antigens (MAA) identified so far is the high molecular weight-melanoma associated antigen (HMW-MAA) with a molecular weight of >1,000,000. Murine antiidiotypic monoclonal antibodies raised against an antibody to HMW-MAA have been disclosed in European Patent Application No. 428 485.

However, a major limitation in the use of said murine-derived antiidiotypic monoclonal antibodies as diagnostic and therapeutic agents is their immunogenicity as foreign proteins, their rather long persistence in the circulation, and the formation of damaging immune complexes. On the other hand, the treatment with human monoclonal antibodies is also limited since human hybridoma cell lines are hard to prepare, generally unstable, and do not produce monoclonal antibodies of appropriate specificity in sufficient quantities and at reasonable costs.

Accordingly, there is a need for antiidiotypic antibodies the application of which inheres a reduced risk of eliciting an undesired anti-murine immunoglobulin immune response, while e.g. the idiotypic immune response and thus the production of endogenous anti-antiidiotypic antibodies should not be affected.

OBJECT OF THE INVENTION

It is an object of the invention to provide such antibodies and methods for the production therof. The antibodies of the invention are antibodies which are obtainable by "humanizing" murine antiidiotypic monoclonal antibodies bearing the internal image of HMW-MAA.

The antibodies of the invention can be used for diagnostic, prophylactic and therapeutic purposes, e.g. for monitoring, control, prevention and treatment of melanoma. The antibodies of the invention have immunregulatory functions such as the stimulation of humoral and cellular immunity.

It is another object of the present invention to provide recombinant DNA molecules encoding the antibodies according to the invention, and methods for the production thereof.

Moreover the invention relates to expression systems suitable for the expression of such recombinant DNA molecules.

DESCRIPTION OF THE INVENTION

Due to the fact that the variable region and each of the constant region domains of immunoglobulin molecules are encoded in separate exons with their own splice sites, recombinant DNA techniques can be used to isolate different parts of cloned immunoglobulin genes and ligate them to parts of other immunoglobulins. The reconstructed genes are expressed by appropriate transformed hosts. Murine antibodies can, for example, be converted into "humanized" antibodies by exchanging murine constant region exons for human immunoglobulin constant region exons, thus generating chimeric antibodies with murine antibody-combining sites and human constant regions. The chimeric antibodies have the antigen specificity determined by the murine variable regions, but also exhibit human effector functions (such as complement binding, stimulation of phagocytosis, triggering of granule release by mast cells) determined by the carboxy-terminal constant region segments of the heavy chain polypeptides.

More specifically, the invention concerns an antiidiotypic monoclonal antibody comprising human constant regions, and variable regions which are the internal image of epitopes on human high molecular weight-melanoma associated antigen (HMW-MAA). This means that the antiidiotypic monoclonal antibody (anti-id MAb) of the invention has constant regions which are obtainable from a human antibody, or that the amino acid sequences of the constant regions are homologous to sequences of a human antibody, and that the anti-id MAb of the invention has variable regions which are obtainable from a monoclonal antiidiotypic internal image-type antibody, e.g. a murine antibody, recognizing (i.e. selectively binding) antibodies (primary Abs-1) directed against HMW-MAA antigen, or that the amino acid sequences of the variable regions are homologous to sequences of such an anti-id MAb.

Antiidiotypic antibodies are directed against the variable region of another antibody molecule, i.e. against particular antibody idiotypes, and are produced by using antibodies as immunogens. Antiidiotypic antibodies are therefore often designated as Ab-2 (antibody 2) while the immunizing antibody is referred to as Ab-1. Antiidiotypic antibodies of the internal image type are reactive with antigen-binding structures on the immunizing antibody (Ab-1) which are complementary to the antigen, i.e. such antibodies (Abs-2) represent the conformational mirror image of the antigen. Internal image antibodies in vitro inhibit the binding of the immunizing antibody (Ab-1) to target cells, and in vivo elicit anti-antiidiotypic antibodies, also designated Ab-3, which are directed against the antigen and have the same, or a very similar, reactivity pattern as Ab-1.

The internal image type-antibodies provided by the present invention mimic the same determinants of HMW-MAA recognized by the immunizing antibodies. They recognize idiotopes within the antigen combining site of the immunizing anti-HMW-MAA monoclonal antibody Ab-1 and therefore inhibit the binding of Ab-1 to melanoma cells expressing HMW-MAA, and induce anti-antiidiotypic antibodies (Ab-3) reactive with HMW-MAA.

The specificity of the antibodies according to the invention for the immunizing anti-HMW-MAA monoclonal antibody (Ab-1), e.g. murine monoclonal antibody 763.74, is tested in an immunoassay, for instance a binding assay in which carriers are coated with Ab-1, incubated with labelled, e.g. radioactively or enzyme-labelled, antiidiotypic monoclonal antibodies of the invention, and the bound label is detected. To investigate whether the antibodies of the invention recognize idiotopes within the antigen combining site of the monoclonal antibody used for immunization, their ability to inhibit the binding of Ab 1 to melanoma cells expressing HMW-MAA is tested, for example in an immunoassay. Such an immunoassay may be a competitive radio- or enzyme immunoassay wherein the labelled, e.g. radioactively or enzyme-labelled, immunizing anti-HMW-MAA monoclonal antibody is incubated with a corresponding antibody of the invention, the mixture is added to HMW-MAA carrying melanoma cells, e.g. cultured melanoma cells Colo 38, and the bound label is measured after further incubation. To ensure that the antibodies of the invention are of the internal image type, it is examined whether they are capable of inducing anti-antiidiotypic antibodies which are reactive with HMW-MAA and exhibit the same reactivity pattern as Ab 1. The induction of anti-anti-idiotypic antibodies can be performed in an animal model, for example in mice. The generated anti-antiidiotypic antibodies are for instance tested for their specificity for HMW-MAA, e.g. in an immunoassay investigating their binding to HMW-MAA carrying melanoma cells, and electrophoretic analysis, for example sodium dodecylsulphate-poly-acrylamide gel electrophoresis (SDS-PAGE), of the antigens immunoprecipitated from the cells. The anti-antiidiotypic antibodies can also be tested for their reactivity with the antibody used for generation.

In particular, the invention concerns antiidiotypic monoclonal antibodies comprising human constant regions, and variable regions which are the internal image of determinants recognized by the monoclonal antibody designated MAb 763.74, and derivatives thereof, or any antibody capable of competing with MAb 763.74 for binding to HMW-MAA, on HMW-MAA. The monoclonal antibody MAb 763.74 is described by P. Giacomini et al. (J. Immunol. 135, 696 (1985)).

Examples of such antiidiotypic monoclonal antibodies are chimeric antibodies comprising human constant regions and variable regions obtainable from the murine monoclonal antibody designated MK2-23. The antiidiotypic antibody MK2-23 has been raised against the murine monoclonal antibody designated 763.74 and is the internal image of determinants recognized by the latter antibody on HMW-MAA.

Most preferred is the chimeric antibody designated MK 2-CHγ1comprising light chain human constant regions κ, heavy chain human constant regions γ and the variable regions of the murine antiidiotypic monoclonal antibody MK2-23, and derivatives of antibody MK 2-CHγ1, preferably fragments, such as Fab-, Fab'-, F(ab')$_2$- and Fv-fragments. The antibody MK2-23 is capable of eliciting antibodies (ABs-3) which mimic the characteristics of the monoclonal antibody 763.74.

Another technique in "humanizing" antibodies described in European Patent Application 0 239 400 exchanges also other fairly conserved regions, the so-called framework regions (FRs), within the murine variable regions for corresponding framework regions from human antibodies. In such a humanized antibody the only parts obtainable from a murine antibody are those hypervariable regions which define a particular specificity for an antigen, the so-called complementarity determining regions (CDRs).

Accordingly, the invention relates to antiidiotypic monoclonal antibodies, and derivatives thereof, comprising light chain variable regions comprising a polypeptide of the formula $$FR_1—CDR_{1L}—FR_2—CDR_{2L}—FR_3—CDR_{3L}—FR_4 \qquad (I)$$

wherein $FR_1$ is a polypeptide residue comprising 19–23 naturally occurring amino acids, $FR_2$ is a polypeptide residue comprising 13–17 naturally occurring amino acids, $FR_3$ is a polypeptide residue comprising 30–34 naturally occurring amino acids, $FR_4$ is a polypeptide residue comprising 7–11 naturally occurring amino acids, $CDR_{1L}$ is a polypeptide residue of the amino acid sequence 22 to 36 of SEQ ID NO:2, $CDR_{2L}$ is a polypeptide residue of the amino acid sequence 52 to 58 of SEQ ID NO:2, and $CDR_{3L}$ is a polypeptide residue of the amino acid sequence 91 to 99 of SEQ ID NO:2, and wherein the amino acid Cys may be in the oxidized state forming S-S-bridges. These particular complementarity determining regions are Arg-Ala-Ser-Glu-Ser-Val-Glu-Tyr-Tyr-Gly-Ser-Ser-Leu-Met-Gln ($CDR_{1L}$ SEQ ID No:10), Ala-Ala-Ser-Asn-Val-Glu-Ser ($CDR_{2L}$ SEQ ID No:11), and Gln-Gln-Ser-Arg-Lys-Ile-Pro-Tyr-Thr ($CDR_{3L}$ SEQ ID No:12).

In particular, the invention relates to monoclonal antibodies comprising light chain variable regions of formula I, wherein the polypeptide residues of the framework regions $FR_1$, $FR_2$, $FR_3$ and $FR_4$ are those preferably occurring in mammalian, especially murine or human, antibodies.

Preferred are monoclonal antibodies according to the invention with light chain variable regions comprising a polypeptide of the amino acid sequence of SEQ ID NO:1, wherein optionally one or more, e.g. 1, 2, 3 or 4, single amino acids within the amino acid sequences 1 to 21 ($FR_1$), 37 to 51 ($FR_2$), 59 to 90 ($FR_3$), and/or 100 to 108 ($FR_4$) are replaced by other amino acids or deleted, and wherein the amino acid Cys may be in the oxidized state forming S-S-bridges, in particular the chimeric monoclonal antibodies and derivatives thereof with light chain variable regions comprising a polypeptide of the amino acid sequence of SEQ ID NO:1, wherein the amino acid Cys may be in the oxidized state forming S-S-bridges.

For example, a hydrophobic amino acid within the framework regions may be replaced by another amino acid, preferably also a hydrophobic amino acid, replaced by two amino acids, or deleted. Likewise, a hydrophilic amino acid within the framework region may be replaced by another amino acid, preferably a hydrophilic acid, two amino acids or deleted, whereby replacing amino acids preferably maintain the hydrogen bond structure of the corresponding framework region.

Likewise preferred antiidiotypic monoclonal antibodies of the invention are those wherein the heavy chain variable regions comprise a polypeptide of the formula

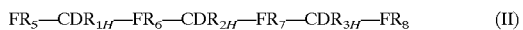
(II)

wherein $FR_5$ is a polypeptide residue comprising 25–29 naturally occurring amino acids, $FR_6$ is a polypeptide residue comprising 12–16 naturally occurring amino acids, $FR_7$ is a polypeptide residue comprising 30–34 naturally occurring amino acids, $FR_8$ is a polypeptide residue comprising 6–10 naturally occurring amino acids, $CDR_{1H}$ is a polypeptide residue of the amino acid sequence 28 to 32 of SEQ ID NO:4, $CDR_{2H}$ is a polypeptide residue of the amino acid sequence 47 to 63 of SEQ ID NO:4, and $CDR_{3H}$ is a polypeptide residue of the amino acid sequence 96 to 109 of SEQ ID NO:4, and wherein the amino acid Cys may be in the oxidized state forming S-S-bridges. These particular complementarity determining regions are Ser-Phe-Gly-Met-His ($CDR_{1H}$ SEQ ID No:13), Tyr-Ile-Ser-Ser-Asp-Ser-Ser-Asn-Ile-Tyr-Tyr-Ala-Asp-Thr-Val-L ys-Gly ($CDR_{2H}$ SEQ ID No:14), and Ser-Asn-Tyr-Val-Gly-Tyr-His-Val-Arg-Trp-Tyr-Phe-Asp-Val ($CDR_{3H}$ SEQ ID No:15).

Especially preferred are monoclonal antibodies comprising heavy chain variable regions of formula II, wherein the polypeptide residues of the framework regions $FR_5$, $FR_6$, $FR_7$ and $FR_8$ are those preferably occurring in mammalian, especially murine or human, antibodies.

Most preferred are monoclonal antibodies and derivatives thereof according to the invention with heavy chain variable regions comprising a polypeptide of the amino acid sequence of SEQ ID NO:4, wherein optionally one or more, e.g. 1, 2, 3 or 4, single amino acids within the amino acid sequences 1 to 27 ($FR_5$), 33 to 46 ($FR_6$), 64 to 95 ($FR_7$), and/or 110 to 117 ($FR_8$) are replaced by other amino acids or deleted, and wherein the amino acid Cys may be in the oxidized state forming S-S-bridges, in particular the chimeric monoclonal antibodies and derivatives thereof with heavy chain variable regions comprising a polypeptide of the amino acid sequence of SEQ ID NO:4, wherein the amino acid Cys may be in the oxidized state forming S-S-bridges. For example, amino acids within the framework regions may be replaced by other amino acids or deleted as detailed above for the light chain.

Light chain variable regions and heavy chain variable regions may comprise an acyl residue at the N-terminal of the amino acid sequence listed in SEQ ID NO:2 and SEQ ID NO:4, respectively, for example formyl or alkanoyl, e.g. palmitoyl, myristoyl or lower alkanoyl, such as acetyl or propionyl.

The class of an antibody (immunoglobulin, Ig) molecule is defined by the heavy chain regions. A monoclonal antibody of the invention may be of any immunoglobulin class, i.e. IgA, IgD, IgE, IgG or IgM. Since different isotypes of antiidiotypic antibodies may have different immune-regulatory action, the antiidiotypic MAbs can be chosen accordingly. A preferential monoclonal antibody according to the invention is an immunoglobulin of class G which comprises light chain human constant regions κ or λ, especially human constant regions κ, and heavy chain human constant regions γ1, γ2, γ3 or γ4, especially human constant regions γ1.

The invention preferentially concerns an antiidiotypic monoclonal antibody, and a derivative thereof, with light chain variable regions of formula I with the preferred meaning, e.g. with the amino acid sequence given in SEQ ID NO:2, wherein the amino acid Cys may be in the oxidized state forming S-S-bridges, light chain human constant regions κ, heavy chain variable regions of formula II with the preferred meaning, e.g. with the amino acid sequence given in SEQ ID NO:4, wherein the amino acid Cys may be in the oxidized state forming S-S-bridges, and heavy chain human constant regions γ1.

Derivatives of an antiidiotypic monoclonal antibody of the invention have the antigenic specificity of said antiidiotypic monoclonal antibody. Examples of such derivatives are antiidiotypic monoclonal antibody fragments and any molecule obtainable from an antibody of the invention, or a fragment thereof, by modification, e.g. chemical modification. For example, depending on its intended use, the molecules of the invention may be modified by the attachment of any of a variety of compounds thus forming a conjugate, either by adsorption or using coupling techniques known in the art Examples of such conjugates include conjugates of the antibody, or of a fragment thereof, with a compound which enhances the antigenicity, with an enzyme, with a fluorescent marker, with a chemiluminescent marker, with a metal chelate, with avidin, with biotin or the like, or radioactively labelled antibodies or fragments.

Antibody fragments of the invention are for example the univalent fragments Fab or Fab', the divalent fragment F(ab')$_2$ or the Fv fragment.

Suitable compounds enhancing the antigenicity of the antibodies of the invention are for example lysine rich proteins with free amino groups available for coupling, especially high molecular weight proteins like bovine serum albumin (BSA; MW 66,200), α-amylase from *Bacillus subtilis* (MW 58,000) or keyhole limpet haemocyanin (KLH; MW >1,000,000) which are commercially available in large quantities. Porcine thyroglobulin, toxins such as tetanus-, cholera- or diphteria-toxins, human serum albumin (HSA), β-2 microglobulin, and the like, may also be used as compounds enhancing antigenicity. Other possible compounds include polysaccharides, natural or synthetic lipopoly-saccharides, synthetic polypeptides such as polylysins, activated membranes, latex particles, bacteria such as Salmonella, and the like. Freund's adjuvant, a water-in-oil emulsion optionally further containing killed mycobacteria, e.g. Bacillus Calmette-Guérin (BCG), may also be used. A preferred compound enhancing antigenicity is a muramyl peptide, in particular the muramyl peptide MTP-PE. Such muramyl peptides and conjugates thereof are disclosed in European Patent Applications 0 003 833 and 0 025 495. Another preferred compound enhancing antigenicity is Alum.

Enzymes used for antibody conjugates of the invention are, for example, horseradish peroxidase, alkaline phosphatase, β-D-galactosidase, glucose oxidase, glucoamylase, carbonic anhydrase, acetylcholinesterase, lysozyme, malate dehydrogenase or glucose-6-phosphate dehydrogenase.

Fluorescent markers conjugated with antibodies or fragments of the invention can be fluorescein, fluorochrome, rhodamine, and the like.

Chemiluminescence markers are e.g. acridinium esters of luminol.

In such conjugates, the antibody or fragment is bound to the conjugation partner directly or by way of a spacer or linker group.

Examples of metal chelates are ethylenediaminetetraacetic acid (EDTA), diethylenetriaminepentaacetic acid (DPTA), 1,4,8,11-tetraazatetradecane, 1,4,8,11-tetraazatetradecane 1,4,8,11 -tetraacetic acid, 1 -oxa4,7,12, 15-tetraazaheptadecane-4,7,12,15-tetraacetic acid, or the like.

Radioactively labelled antibodies or fragments of the invention contain e.g. radioactive iodine ($^{123}$I, $^{125}$I, $^{131}$I), tritium ($^3$H), carbon ($^{14}$C), sulfur ($^{35}$S), yttrium ($^{90}$Y), technetium ($^{99m}$Tc), or the like.

The invention further concerns a method for the manufacture of the antibodies, and the derivatives thereof, according to the invention.

The antiidiotypic monoclonal antibody, and a derivative thereof, according to the invention is prepared by a process that is known per se, characterized in that suitable host cells as defined further below producing a protein of the invention, are multiplied in vitro or in vivo and, if required, the desired protein is isolated and optionally converted into a derivative thereof. A protein of the invention can be prepared by a process comprising culturing any suitable transformable host useful in the art under conditions which allow the expression of said protein, isolating said protein and optionally converting the isolated protein into a derivative therof, e.g. by proteolytic cleavage or by attachment of another compound, e.g. a protein or a non-proteinaceous molecule, as mentioned above.

Suitable host cells include eukaryotic cells, e.g. animal cells, plant cells and fungi, and prokaryotic cells, such as gram-positive and gram-negative bacteria, e.g. E. coli. Preferred eukaryotic host cells are cells of mammalian origin and yeast cells.

As used hereinbefore or hereinafter, in vitro means ex vivo, thus including e.g. cell culture and tissue culture conditions.

For example, multiplication of mammalian cells in vitro is carried out in suitable culture media, which are the customary standard culture media, such as Dulbecco's Modified Eagle Medium (DMEM) or RPMI 1640 medium, optionally replenished by a mammalian serum, e.g. fetal calf serum, or trace elements and growth sustaining supplements, e.g feeder cells such as normal mouse peritoneal exudate cells, spleen cells, bone marrow macrophages, 2-aminoethanol, insulin, transferrin, low density lipoprotein, oleic acid, or the like.

In vitro production provides relatively pure antibody preparations and allows scale-up to give large amounts of the desired antibodies. Techniques for bacterial cell, yeast and mammalian cell cultivation are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges.

Large quantities of the desired antiidiotypic monoclonal antibodies of the invention can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl pentadecane), prior to the injection. After one to three weeks, the antibodies are isolated from the body fluids of those mammals. For example, transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The cell culture supernatants are screened for the desired antiidiotypic monoclonal antibodies, preferentially with an enzyme immunoassay, e.g. a sandwich assay or a dot-assay, or a radioimmunoassay. For example, a sandwich enzyme immunoassay may be used to determine whether correctly assembled immunoglobulins are present in cell culture supernatants, whereby an antibody directed to the light chain human constant region κ or λ (as appropriate) and another antibody directed to the heavy chain human constant region γ of the desired subclass are used, one of which is coated to a solid support and the other one conjugated to an enzyme allowing detection with a suitable enzyme substrate. For the determination whether cell supernatants contain antiidiotypic antibodies of the desired specificity, a sandwich enzyme immunoassay may be used comprising the idiotype (Ab-1), e.g. the monoclonal antibody 763.74, coated to a solid support and an enzyme conjugated antibody directed to the appropriate light chain or, preferably, heavy chain constant region.

For isolation of the antiidiotypic monoclonal antibodies, the immunoglobulins in the culture supernatants or in the ascitic fluid may be concentrated, e.g. by precipitation with ammonium sulphate, dialysis against hygroscopic material such as PEG, filtration through selective membranes, or the like. If necessary and/or desired, the antibodies are purified by the customary chromatography methods, for example gel filtration, ion-exchange chromatography, hydrophobic interaction chromatography or affinity chromatography, e.g. immunoaffinitychromatography. Preferably, the antiidiotypic monoclonal antibodies are isolated from cell supernatants containing them by a procedure comprising affinity chromatography, for example with Protein A, ion-exchange chromatography, and/or gel filtration.

Fragments of the antiidiotypic monoclonal antibodies, for example Fab, Fab' or $F(ab')_2$ fragments, can be obtained from the antibodies prepared as described above by methods known per se, e.g. by digestion with enzymes such as papain or pepsin and/or cleavage of disulfide bonds by chemical reduction, or by recombinant DNA techniques.

The antiidiotypic monoclonal antibody derivatives of the invention with enhanced antigenicity are prepared by methods known per se, either by adsorption of an antibody or fragment of the invention to the compound enhancing the antigenicity or by coupling providing chemically bound conjugates. Conjugates of antibodies or fragments of the invention with the mentioned immunogenic compounds or with enzymes are prepared e.g. by reacting an antibody or fragment prepared as described above with the immunogenic compound or the enzyme in the presence of a coupling agent, e.g. glutaraldehyde, periodate, N,N'-o-phenylenedimaleimide, N-(m-maleimidobenzoyloxy)-succinimide, N-(3-[2'-pyridyldithio]-propionoxy)-succinimide, N-ethyl-N'-(3-dimethylamino-propyl)-carbodiimide or the like. Conjugates with biotin are prepared e.g. by reacting antibodies or fragments with an activated ester of biotin such as the biotin N-hydroxy-succinimide ester. Conjugates with fluorescent or chemiluminescent markers are prepared in the presence of a coupling agent, e.g. those listed above, or by reaction with an isothiocyanate, preferably fluorescein-isothiocyanate.

Antiidiotypic monoclonal antibodies or fragments radioactively labelled with iodine ($^{123}I$, $^{125}I$, $^{131}I$) are obtained from the antibodies or fragments of the invention by iodination known pe se, for example with radioactive sodium or potassium iodide and a chemical oxidizing agent, such as sodium hypochlorite, chloramine T or the like, or an enzymatic oxidizing agent, such as lactoperoxidase, or glucose oxidase and glucose. Antibodies or fragments according to the invention are coupled to yttrium ($^{90}Y$) for example by diethylenetriaminepentaacetic acid (DPTA)-chelation. Technetium-99 m labelled antibodies or fragments are prepared by ligand exchange processes, for example by reducing pertechnate ($TcO_4^-$) with stannous ion solution, chelating the reduced technetium onto a Sephadex column and applying the antibodies or fragments to this column, or by direct labelling techniques, e.g. by incubating pertechnate, a reducing agent such as $SnCl_2$, a buffer solution such as sodium-potassium phthalate solution, and the antibodies or fragments.

Fragments and conjugates of antibodies or fragments with compounds enhancing antigenicity or enzymes may also be prepared directly by recombinant DNA techniques, e.g. those described below.

The invention also concerns the invention relates to recombinant DNAs comprising an insert coding for a light chain variable region and/or for a heavy chain variable region of an antibody comprising human constant regions, and varaible regions which are the internal image of epitopes on HMW-MAA. By definition such DNAs comprise coding single stranded DNAs, double stranded DNAs consisting of said coding DNAs and of complementary DNAs thereto, or these complementary (single stranded) DNAs themselves.

More specifically, the invention relates to recombinant DNAs comprising an insert coding for a light chain variable region and/or for a heavy chain variable region of an antibody of the invention the variable regions of which are the internal image of determinants recognized by the monoclonal antibody designated Mab 763.74, and derivatives therof, or any antibody capable of competing with Mab 763.74 for binding to HMW-MAA, on HMW-MAA.

In particular, the invention concerns a recombinant DNA comprising an insert coding for a light chain variable region which is obtainable from genomic DNA of the hybridoma cell line MK2-23, or which is homologous to genomic DNA of said cell line and codes for an amino acid sequence homologous to the light chain variable region of monoclonal antibody MK2-23. The hybridoma cell line MK2-23 was generated by fusion of a mouse myeloma cell and a B lymphocyte of a Balb/c mouse which had been immunized with the murine monoclonal antibody 763.74 (P. Giacomini et al., J. Immunol. 135, 696, 1985). The cell line MK2-23 produces the murine antiidiotypic monoclonal antibody MK2-23 which is the internal image of determinants recognized by the murine monoclonal antibody 763.74 on HMW-MAA.

The invention relates to a recombinant DNA comprising an insert coding for the polypeptide of formula I, wherein $FR_1$, $FR_2$, $FR_3$, $FR_4$, $CDR_{1L}$, $CDR_{2L}$, and $CDR_{3L}$ have the meanings as mentioned hereinbefore, optionally further containing introns. Especially preferred is a recombinant DNA coding for the polypeptide of formula I comprising inserts coding for murine or human framework regions $FR_1$, $FR_2$, $FR_3$ and $FR_4$, and inserts coding for complementarity determining regions of the DNA sequence 70 to 114 ($CDR_{1L}$), the DNA sequence 163 to 180 ($CDR_{2L}$), and the DNA sequence 277 to 303 ($CDR_{3L}$) of SEQ ID NO:1. Most preferred is a DNA comprising an insert of the DNA sequence 7 to 334 of SEQ ID NO:1, wherein optionally one or more, e.g. 1 to 10, nucleotides are replaced by other nucleotides, in particular a DNA comprising an insert of the DNA sequence 7 to 334 of SEQ ID NO:1. In a DNA wherein nucleotides of the sequence given in SEQ ID NO:1 are replaced by other nucleotides, such replacement is preferred when it does not alter the amino acid sequence of the complementarity determining regions (CDRs) coded for. This means that such replacement of nucleotides may occur in the inserts coding for the framework regions (FRs) or in a position where it does not alter the amino acid coded for due to the degeneracy of the triplet codons.

Likewise the invention concerns a recombinant DNA comprising an insert coding for a heavy chain variable region, which is obtainable from genomic DNA of the hybridoma cell line MK2-23 or which is homologous to genomic DNA of said cell line and codes for an amino acid sequence homologous to the heavy chain variable region of monoclonal antibody MK2-23.

The invention relates to a recombinant DNA comprising an insert coding for the polypeptide of formula II, wherein $FR_5$, $FR_6$, $FR_7$, $FR_8$, $CDR_{1H}$, $CDR_{2H}$, and $CDR_{3H}$ have the meanings as mentioned hereinbefore, optionally further containing introns. Especially preferred is a recombinant DNA coding for the polypeptide of formula II comprising inserts coding for murine or human framework regions $FR_5$, $FR_6$, $FR_7$ and $FR_8$, and inserts coding for complementarity determining regions of the DNA sequence 90 to 104 ($CDR_{1H}$), the DNA sequence 147 to 197 ($CDR_{2H}$), and the DNA sequence 294 to 335 ($CDR_{3H}$) of SEQ ID NO:3. Most preferred is a DNA comprising an insert of the DNA sequence 9 to 368 of SEQ ID NO:3, wherein optionally one or more, e.g. 1 to 10, nucleotides are replaced by other nucleotides, in particular a DNA comprising an insert of the DNA sequence 9 to 368 of SEQ ID NO:3. In a DNA wherein nucleotides of the sequence given in SEQ ID NO:3 are replaced by other nucleotides, such replacement is preferred when it does not alter the amino acid sequence of the complementarity determining regions (CDRs) coded for, as is described above for DNA coding for the light chain variable region.

For the assembly of complete tetrameric immunoglobulin molecules and the expression of active antibodies, the recombinant DNA inserts coding for light and heavy chain variable regions are fused with the corresponding DNAs coding for light and heavy chain human constant regions, then transferred into appropriate host cells, for example after incorporation into vectors.

The invention therefore also concerns recombinant DNAs comprising an insert coding for a light chain variable domain as described hereinbefore, fused to a human constant region κ or λ. Preferred is a recombinant DNA coding for a preferred variable region as described hereinbefore fused to a human constant region κ.

Likewise the invention concerns recombinant DNAs comprising an insert coding for a heavy chain variable region as decribed hereinbefore, fused to a human constant region γ, for example γ1, γ2, γ3 or γ4. Preferred is a recombinant DNA coding for a preferred variable region as described hereinbefore, fused to a human constant region γ1.

The invention further concerns recombinant DNAs coding for fragments of antiidiotypic monoclonal antibodies as defined hereinbefore, e.g. DNA coding for Fab, Fab' or Fv fragments of such antibodies, and for conjugates of antibodies or fragments as defined hereinbefore, e.g. for fusion proteins comprising a light and/or heavy chain of such antibody fused to a compound enhancing antigenicity as defined hereinbefore or fused to an enzyme.

Furthermore the invention concerns a recombinant DNA which is a hybrid vector comprising an insert coding for a light chain variable domain and/or heavy chain variable domain.

Preferred hybrid vectors of the invention comprise an insert coding for a light chain as descibed hereinbefore, particularly a chimeric murine/human light chain, and/or an insert coding for a heavy chain, preferably a chimeric murine/human heavy chain as described hereinbefore.

Preferably, the hybrid vector of the invention comprises an above-described insert operably linked to an expression control sequence, inparticular those described hereinafter.

The hybrid vectors of the invention optionally comprise an origin of replication or an autonomously replicating sequence, one or more dominant marker sequences and, optionally, expression control sequences, signal sequences and additional restriction sites.

Vectors typically perform two functions in collaboration with compatible host cells. One function is to facilitate the cloning of the nucleic acid that encodes the immunoglobulin chain, i.e. to produce usable quantities of the nucleic acid (cloning vectors). The other function is to provide for replication and expression of the gene constructs in a suitable host, either by maintenance as an extrachromosomal element or by integration into the host chromosome (expression vectors). A cloning vector comprises the gene constructs as described above, an origin of replication or an autonomously replicating sequence, selectable marker sequences and, optionally, signal sequences and additional restriction sites. An expression vector additionally comprises expression control sequences essential for the transcription and translation of the genes.

An origin of replication or an autonomously replicating sequence is provided either by construction of the vector to include an exogeneous origin such as derived from Simian virus 40 (SV 40) or another viral source, or by the host cell chromosomal mechanisms.

The markers allow for selection of host cells which contain the vector. Selection markers include genes which confer resistance to heavy metals such as copper or to antibiotics such as tetracycline, ampicillin, geneticin (G-418), neomycin, kanamycin or hygromycin, or genes which complement a genetic lesion of the host cell such as the absence of thymidine kinase, hypoxanthine phosphoryl transferase, dihydrofolate reductase or the like.

Signal sequences may be, for example, presequences or secretory leaders directing the secretion of the antibody, splice signals, or the like.

As expression control sequences, the vector DNA comprises a promoter, sequences necessary for the initiation and termination of transcription and for. stabilizing the mRNA and, optionally, enhancers and further regulatory sequences.

A wide variety of promoting sequences may be employed, depending on the nature of the host cell. Promoters that are strong and at the same time well regulated are the most useful. Sequences for the initiation of translation are for example Shine-Dalgarno sequences. Sequences necessary for the initiation and termination of transcription and for stabilizing the mRNA are commonly available from the noncoding 5'-regions and 3'-regions, respectively, of viral or eukaryotic cDNAs, e.g. from the expression host. Enhancers are transcription-stimulating DNA sequences of viral origin, e.g. derived from Simian virus, polyoma virus, bovine papilloma virus or Moloney sarcoma virus, or of genomic, especially murine, origin.

The various DNA segments of the vector DNA are operationally Linked, i.e. they are contiguous and placed into a functional with each other.

Examples of vectors which are suitable for replication and expression in an *E. coli* strain are bacteriophages, for example derivaitves of λ bacteriophages, or plasmids. Suitable vectors contain a complete replicon, a marker gene, recognition sequences for restriction endonucleases, so that the foreign DNA and, if appropriate, the expression control sequence can be inserted at these sites, and optionally signal sequences and enhancers.

Microbial promoters are, for example, the strong leftward promoter $P_L$ of bacteriophage λ which is controlled by a temperature sensitive repressor. Also suitable are *E. coli* promoters such as the lac (lactose) promoter regulated by the lac repressor and induced by isopropyl-β-D-thiogalactoside, the trp (tryptophan) promoter regulated by the trp repressor and induced e.g. by tryptophan starvation, and the tac (hybrid trp-lac promoter) regulated by the lac repressor.

Vectors which are suitable for replication and expression in yeast contain a yeast replication start and a selective genetic marker for yeast. One group of such vectors includes so-called ars sequences (autonomous replication sequences) as origin of replication. These vectors are retained extrachromosomally within the yeast cell after the transformation and are replicated autonomously. Furthermore, vectors which contain all or part of the 2 μ (2 mikron) plasmid DNA from *Saccharomyces cerevisiae* can be used. Such vectors will get integrated by recombination into 2 μ plasmids already existing within the cell, or replicate autonomously. 2μ sequences are particularly suitable when high transformation frequency and high copy numbers are to be achieved.

Expression control sequences which are suitable for expression in yeast are, for example, those of highly expressed yeast genes. Thus, the promoters for the TRP1 gene, the ADHI or ADHII gene, acid phosphatase (PHO3 or PHO5) gene, isocytochrome gene or a promoter involved with the glycolytic pathway, such as the promoter of the enolase, glyceraldehyde-3-phosphate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, can be used.

Promoters suitable for mammalian host cells are obtained from viruses such as Simian virus 40 (SV 40), Rous sarcoma virus (RSV), adenovirus 2, bovine papilloma virus (BPV), papovavirus BK mutant (BKV), or mouse or human cytomegalovirus (CMV). Alternatively, the vectors may comprise promoters from mammalian expression products, such as actin, collagen, myosin etc., or the native promoter and control sequences which are normally associated with the immunoglobulin gene sequences.

The vectors may be suitable for both procaryotic and eucaryotic hosts.

The gene constructs for the light chain and for the heavy chain are sequentially or simultaneously transferred into the host cells with the help of two vectors. Alternatively, both heavy and light chains are cloned into the same hybrid vector and incorporated in a one step-procedure as a single construct into the host cells. A third alternative utilises co-transfection of unlinked DNA fragments.

The recombinant DNAs coding for the desired antiidiotypic monoclonal antibodies can be prepared, for example, by culturing a transformed host cell.

In particular, such DNAs can be prepared by a method comprising a) preparing DNA coding for the variable heavy and/or light chain variable domain bearing the internal image of HMW-MAA, e.g. by isolating DNA from the genome of a suitable hybridoma cell line and selecting the desired DNA using DNA probes, or by isolating mRNA from a suitable hybridoma cell line and preparing cDNA coding for the desired heavy and/or light chain domain;

b) preparing DNA coding for the heavy and/or light chain constant region of a human antibody, e.g. by isolating DNA from a genomic library and selecting the desired DNAs coding for said constant regions of antibodies using DNA probes;

c) constructing the desired genes by incorporating the DNA of step a) and b) into appropriate hybrid vectors;

d) transferring the obtained hybrid vectors into a recipient host cell or retrieving the DNA coding for the desired genes and transferring the unlinked DNA into a suitable recipient host cell, e) selecting and culturing the transformed host cell, and f) optionally isolating the desired DNA.

The DNA according to step a) of the process described above can be obtained by isolation of genomic DNA or by preparation of cDNA from isolated mRNA. Genomic DNA from hybridoma cells is isolated by methods known in the art which include steps for disruption of the cells, e.g. by lysis in presence of detergents like Triton™, extracting the DNA, e.g. by treatment with phenol and $CHCl_3$/isoamyl alcohol, and precipitation of DNA. The DNA is fragmented, conveniently by one or more restriction endonucleases, e.g. XbaI, BglII, EcoRI, HindIII, BamHI, the resulting fragments are replicated on a suitable carrier, e.g. nitrocellulose membranes, and screened with a DNA probe as described in more detail hereinbelow for the presence of the DNA sequences coding for the polypeptide sequence of interest, in particular for the presence of the rearranged H- and L-chain Ig gene loci. By this procedure DNA fragments are found that contain inserts with heavy chain V, D and J regions and light chain V and J regions, respectively, together with a leader sequence and introns, if any. cDNA from hybridoma cells is likewise prepared by methods known in the art, e.g. by extracting total cellular RNA, isolating mRNA by a suitable chromatographic method, e.g. chromatography on oligo(dT)-cellulose, synthesizing cDNA with a mixture of deoxynucleotide triphosphate and reverse transcriptase in the presence of oligonucleotide primers complementary to suitable regions in the murine immunoglobulin heavy and light chain constant genes, and isolating the cDNA. As a tool simplifying DNA isolation, the desired genomic DNA or cDNA may be amplified using polymerase chain reaction (PCR) technology. PCR involves repeated rounds of extension from two primers specific for DNA regions at each end of the gene. Preferably, cDNA transcripts of total mRNA from the suitable hybridoma cell line is treated in a heating/cooling cycle with Taq DNA polymerase in the presence of primers tailored to hybridize to Ig H and L chain variable regions, respectively.

Genomic human DNA according to step b) of the process described above is isolated from suitable human tissue, preferably from human placenta or human foetal liver cells, according to methods known in the art A genomic DNA library is constructed therefrom by limited digestion with suitable restriction endonucleases, e.g. HaeM and AluI, and incorporation into λ Charon phage, e.g. λ Charon 4a, following established procedures. The genomic DNA library is replicated, e.g. on nitrocellulose membranes, and screened with a DNA probe as described below for the DNA sequences of interest. The desired DNA may be amplified using PCR technology.

The DNA probe for the mouse variable regions or the human constant regions may be a synthetic DNA, a cDNA derived from mRNA coding for the desired immunoglobulin or a genomic DNA or DNA fragment of known nucleotide sequence. As probes for the detection and/or amplification of the rearranged Ig gene loci of the variable regions of L-/H-chains, DNA fragments of known nucleotide sequences of adjacent conserved variable or constant regions are selected which constitute the Ig loci of the L-/H-chain in the mammal from which the DNA is derived, e.g. Balb/c mice. The possible utilization of murine DNA probes for the detection of human DNA sequences is based on sequence homologies between the murine and human DNAs. The DNA probe is synthesized or isolated from suitable tissue of an appropriate mammal, e.g. Balb/c mouse liver, and purified by standard methods. If required, the probe DNA is labelled, e.g. radioactively labelled by the well-known nick-translation technique, then hybridized with the human DNA library in buffer and salt solutions containing adjuncts, e.g. calcium chelators, viscosity regulating compounds, proteins, non-specific DNA and the like, at temperatures favoring selective hybridization.

Once a fragment has been identified which contains the desired DNA sequence, this fragment may be further manipulated to remove nonessential DNA, modified at one or both termini, and treated to remove all or a portion of intervening sequences, or the like.

The joining of the various DNA fragments in order to produce the desired genes is performed in accordance with conventional techniques, for example, by blunt- or staggered-end ligation, restriction enzyme digestion to provide for appropriate cohesive termini, filling in cohesive ends as appropriate, alkaline phosphatase treatment to avoid undesirable joining, and ligation with appropriate ligases.

The transfer of the recombinant DNAs, e.g. the transfer of hybrid vectors, and the selection of transformed cells is described below. Moreover, the invention relates to a suitable host cell transformed with the recombinant DNAs described above, namely a host cell which is transformed with a DNA encoding the light chain and/or a DNA encoding the heavy chain of the desired antiidiotypic monoclonal antibody of the invention.

The host cells of the present invention have to be capable of culture in vitro. Suitable host cells are of prokaryotic or eukaryotic origin and include bacterial cells, particularly *E. coli*, yeasts, e.g. *Saccharomyces cerevisiae*, or mammalian cells. To provide a suitable environment for the production of functional tetrameric antibodies, host cells of eukaryotic, particularly mammalian or yeast origin are preferred since the biosynthesis of functional tetrameric antibody molecules requires correct nascent polypeptide chain folding and assembly. Prokaryotic hosts, especially *E.coli*, may be used for the production of antibody fragments of the invention, e.g. Fab- and Fv-fragments.

Examples of suitable hosts are microorganisms which are devoid of or poor in restriction or modification enzymes, such as bacteria, in particular strains of *Escherichia coli*, and yeasts, for example *Saccharomyces cerevisiae*.

The most preferred host cells according to the invention are mammalian cells, e.g. COS-7 cells, Bowes melanoma cells, chinese hamster ovary (CHO) cells, embryonic lung cells L-132, and in particular mammalian cells of lymphoid origin, such as lymphoma, myeloma, hybridoma, trioma or quadroma cells, for example PAI, Sp2/0 or X63-Ag8.653 cells. Preferred are cells of the cell line Sp2/0, which is a well-characterized, Ig non-secreting mouse cell line derived from the fusion of mouse spleen cells with the myeloma X63-Ag8.

These host cells are transfected with the L-chain gene construct alone, with the H-chain gene construct alone, or with both, either sequentially or simultaneously transferred with the help of two separate vectors or in a one-step procedure by using a double-construct (L-chain/ H-chain) vector as indicated hereinbefore. In the alternative, unlinked gene constructs may be transfected into the host cells either sequentially or simultaneously.

Preferred are host cells transfected with both gene constructs secreting antiidiotypic monoclonal antibodies as described hereinbefore, for example cells of the cell line MK2-CHγ1. Further examples of host cells of the invention are cells transfected with similar recombinant plasmids which contain alternative orientations of the H- and L-chain gene constructs, incorporating additional DNA elements to facilitate high levels of expression of the monoclonal antibodies of the invention.

The host cells of the invention are genetically stable, produce and preferably secrete antiidiotypic monoclonal antibodies of the invention of constant specificity and can be activated from deep-frozen cultures by thawing and recloning.

The transformed host cells are cultured by methods known in the art in a liquid medium containing assimilable sources of carbon, e.g. carbohydrates such as glucose or lactose, nitrogen, e.g. amino acids, peptides, proteins or their degradation products such as peptones, ammonium salts or the like, and inorganic salts, e.g. sulfates, phosphates and/or carbonates of sodium, potassium, magnesium and calcium. The medium furthermore contains, for example, growth-promoting substances, such as trace elements, for example iron, zinc, manganese and the like.

The medium is preferably chosen as to exert a selection pressure and prevent the growth of cells which have not been transformed or have lost the hybrid vector. Thus, for example, an antibiotic is added to the medium if the hybrid vector contains an antibiotic resistance gene as marker. If, for instance, a host cell is used which is auxotrophic in an essential amino acid whereas the hybrid vector contains a gene coding for an enzyme which complements the host defect, a minimal medium deficient of said amino acid is used to culture the transformed cells.

Culturing is effected by processes which are known in the art. The culture conditions, such as temperature, pH value of the medium and fermentation time, are chosen so that a maximum titer of the polypeptide or derivative of the invention is obtained. Thus, an E. coli or yeast strain is preferably cultured under aerobic conditions by submerged culture with shaking or stirring at a temperature of about 20° C. to 40° C., preferably at about 30° C., and a pH value of 4 to 8, preferably of about pH 7, for about 4 to 30 hours, preferably until maximum yields of the polypeptide or derivative of the invention are reached.

When the cell density has reached a sufficient value, the culture is interrupted and the polypeptide or derivative can be isolated. If the hybrid vector contains a suitable secretion signal sequence, the polypeptide or derivative is secreted by the transformed cell directly into the culture medium. Otherwise, the cells have to be destroyed, for example by treatment with a detergent such as SDS, NP-40™, Triton™ or deoxycholic acid, lysed with lysozyme or a similarly acting enzyme, or disrupted by an osmotic shock or ultra-sound. Break-up of the cells will also be required if the signal sequence directs the secretion of the desired protein into the cell periplasm. If yeast is used as a host microorganism, the cell wall may be removed by enzymatic digestion with a glucosidase. Alternatively or additionally, mechanical forces, such as shearing forces (e.g. French press, Dyno mill and the like) or shaking with glass beads or aluminium oxide, or alternating freezing, for example in liquid nitrogen, and thawing, for example at 30° C. to 40° C., as well as ultra-sound can be used to break the cells.

The cell supernatant or the solution obtained after centrifugation of the mixture obtained after breaking the cells, which contains proteins, nucleic acids and other cell constituents, is enriched in proteins, including the polypeptides of the invention, in a manner which is known per se. Thus, for example, most of the non-protein constituents are removed by polyethyleneimine treatment and the proteins including the polypeptides and derivatives of the invention are isolated e.g. by the methods mentioned above.

The invention also relates to processes for the preparation of transformed host cells characterized in that suitable recipient host cells as described hereinbefore are transformed with one or two vectors according to the invention, and the transformed cells are selected.

Transformation of microorganisms is carried out as described in the literature, for example for S. cerevisiae (A. Hinnen et al., Proc. Natl. Acad. Sci. USA 75: 1929, 1978), and for E. coli (M. Mandel et al., J. Mol. Biol. 53: 159, 1970).

Accordingly, the transformation procedure of E. coli cells includes, for example, $Ca^{2+}$ pretreatment of the cells so as to allow DNA uptake, and incubation with the hybrid vector. The subsequent selection of the transformed cells can be achieved, for example, by transferring the cells to a selective growth medium which allows separation of the transformed cells from the parent cells dependent on the nature of the marker sequence of the vector DNA. Preferably, a growth medium is used which does not allow growth of cells which do not contain the vector. The transformation of yeast comprises, for example, steps of enzymatic removal of the yeast cell wall by means of glucosidases, treatment of the obtained spheroplasts with the vector in the presence of polyethylene glycol and $Ca^{2+}$ ions, and regeneration of the cell wall by embedding the spheroplasts into agar. Preferably, the regeneration agar is prepared in a way to allow regeneration and selection of the transformed cells as described above at the same time.

Transformation of cells of higher eukaryotic origin, such as mammalian cell lines is preferably achieved by transfection. Transfection is carried out by conventional techniques, such as calcium phosphate precipitation, microinjection into the cell nucleus, protoplast fusion, electroporation, i.e. introduction of DNA by a short electrical pulse which transiently increases the permeability of the cell membrane, or the like. Transfection may be carried out in the presence of helper compounds, e.g. diethylaminoethyldextran, dimethyl sulfoxide, glycerol, polyethylene glycol or the like, or as co-precipitates of vector DNA and calcium phosphate.

After the transfection procedure, transfected cells are identified and selected with the help of a selection procedure matching the selection marker of the DNA used for transfection. Selection markers include genes which confer resistance to heavy metals such as copper or to antibiotics, e.g. G-418 (geneticin, a neomycin-derivative) or hygromycin, or genes which complement a genetic lesion of the host cell such as the absence of thymidine kinase, hypoxanthine phosphoribosyl transferase, dihydrofolate reductase, or the like. For example, if the DNA used for transfection comprises a marker for geneticin resistance, transformed cells are identified and separated from untransformed cells by culture in the presence of the antibiotic geneticin.

The antiidiotypic monoclonal antibodies and their derivatives according to the invention are useful for a number of prophylactic, therapeutic and diagnostic purposes. In particular, the invention concerns a method of treating melanoma by modulation of the immune response to HMW-MAA.

Active immunotherapy comprises the induction of antibody and/or T-cell responses in a patient or animal. In active immunotherapy, an antibody of the invention may be administered in order to heighten the immune response to stimulate the beneficial components of the immune system; for example, in treatment of melanoma it is desirable to elicit humoral and cellular responses directed against HMW-MAA.

The antiidiotypic monoclonal antibodies and their derivatives according to the invention can, for example, be used to modulate the immune response to HMW-MAA due to their immune-regulatory functions within the idiotype-antiidiotype reaction network. The modulation is specific and is determined by the choice of the antibody (Ab-1) used for the production of the murine antiidiotypic monoclonal antibodies from which the variable regions are derived, i.e. the specificity of the immunizing Ab-1, and by the isotype of the antibody of the invention, since different isotypes of antiidiotypic antibodies have different immune-regulatory functions. The chance of an adverse immunological response to the antibody of the invention as such is considerably reduced in comparison with adverse reactions caused by repeated application of comparable murine or other non-human antibodies. As the antibodies of the invention are of the internal image type they are capable of eliciting antibodies (Abs-3) directed against HMW-MAA (active immunotherapy). These elicited antibodies have the same general reactivity pattern as the antibody (Ab-1) originally used for immunization. The stimulation of endogenous production of antibodies (Abs-3) directed against HMW-MAA overcomes the drawbacks of direct application of such immunizing antibodies (Abs-1) in a passive immunotherapy, i.e. the necessity of a great number of injections and large doses.

The Mabs of the invention can be "tailor-made" to mimic specific determinants of HMW-MAA by the adequate choice of the immunizing antibody. Consequently, the antiidiotypic monoclonal antibodies and derivatives thereof according to the invention, in particular fragments and conjugates with compounds enhancing antigenicity, are useful agents for the control and treatment of melanoma, that is to say that they can be successfully employed, e.g. to cause tumor regression and/or prevent tumor recurrence.

Moreover, the antiidiotypic MAbs of the invention are useful for preventing melanoma by induction of immunity against the determinants of high molecular weight-melanoma associated antigen recognized by the immunizing monoclonal antibody.

The invention also concerns pharmaceutical compositions comprising a antiidiotypic monoclonal antibody and/or a derivative thereof according to the invention. The pharmaceutical compositions comprise, for example, the antiidiotypic monoclonal antibodies and/or derivatives thereof in a therapeutically effective amount together or in admixture with a pharmaceutically acceptable carrier. Derivatives of antibodies that are considered are fragments or conjugates with compounds enhancing antigenicity.

Preferred are pharmaceutical compositions for parenteral application and inhalation, e.g. nasal application. Compositions for intramuscular, subcutaneous or intravenous application or for inhalation are e.g. isotonic aqueous solutions or suspensions, optionally prepared shortly before use from lyophilized or concentrated preparations. Suspensions in oil contain as oily component the vegetable, synthetic or semi-synthetic oils customary for injection purposes. The pharmaceutical compositions may be sterilized and contain adjuncts, e.g. for conserving, stabilizing, wetting, emulsifying or solubilizing the ingredients, salts for the regulation of the osmotic pressure, buffer and/or compounds regulating the viscosity, e.g. sodium carboxycellulose, carboxymethylcellulose, sodium carboxymethylcellulose, dextran, polyvinylpyrrolidine or gelatine.

Preferred are pharmaceutical compositions further comprising adjuvants which positively influence the formation of endogenous antibodies (Abs-3). Adjuvants considered are complete Freund's adjuvant (emulsion of mineral oil, water, and mycobacterial extracts), incomplete Freund's adjuvant (emulsion of water and oil only), mineral gels, e.g. aluminium hydroxide gels, surface active substances such as lysolecithin, polyanions, peptides, BCG (Bacillus Calmette-Guérin), or the compounds enhancing antigenicity mentioned above. Particularly preferred are the muramyl peptide MTP-PE or Alum. If the pharmaceutical composition contains conjugates of antibodies or fragments of the invention with compounds enhancing antigenicity, no further adjuvants may be required.

The pharmaceutical compositions are prepared by methods known in the art, e.g. by conventional mixing, dissolving or lyophilizing, and contain from approximately 0.01% to approximately 50% of active ingredients. They may be in dosage unit form, such as ready-to-use ampoules or vials, or also in lyophilized solid form.

The specific mode of administration and the dosage will be selected by the attending physician taking into account the particulars of the patient, the state of the disease, the type of melanoma treated, and the like. The therapeutic dose for mammals is between approximately 30 $\mu$g and 100 $\mu$g of antiidiotypic monoclonal antibodies of the invention and/or derivatives therof per kg body weight depending on the status of the patient and the mode of application.

The pharmaceutical compositions of the invention are prepared by methods known in the art, e.g. by conventional mixing, dissolving, confectioning or lyophilizing processes. Pharmaceutical compositions for injection are processed, filled into ampoules or vials, and sealed under aseptic conditions according to methods known in the art The antiidiotypic MAbs and derivatives thereof according to the invention can also be used for the qualitative and quantitative determination of antibodies directed against HMW-MAA. This is especially useful for the monitoring of melanoma, for the diagnosis of melanoma, for the decision whether a disease is amenable to treatment with the antiidiotypic monoclonal antibodies of the invention, and for monitoring the treatment of the disease with the antiidiotypic monoclonal antibodies and derivatives thereof. As the antibodies of the invention eliminate the immunological response e.g. to murine constant regions, their use for in vivo diagnosis is particularly beneficial.

In general, the antiidiotypic monoclonal antibodies or derivatives thereof according to the invention can be used in any of the known immunoassays which rely on the binding interaction between the idiotopes of the antibodies directed against HMW-MAA and of the antiidiotypic antibodies. Examples of such assays are radio-, enzyme, fluorescence, chemiluminescence, immunoprecipitation, latex agglutination, and hemagglutination immunoassays.

The antiidiotypic monoclonal antibodies according to the invention can be used as such or in the form of radioactively labelled derivatives in a radioimmunoassay (RIA). Any of the known modifications of a RIA can be used, for example soluble phase (homogeneous) RIA, solid phase (heterogeneous) RIA, single RIA or double (sandwich) RIA with direct or indirect (competitive) determination of antibodies directed against HMW-MAA.

An example of such a radioimmunoassay is a sandwich RIA in which a suitable carrier, for example the plastic surface of a microtiter plate or of a test tube, e.g. of polystyrene, polypropylene or polyvinylchloride, glass or plastic beads, filter paper, dextran etc. cellulose acetate or nitrocellulose sheets, magnetic particles or the like, is coated with an antiidiotypic monoclonal antibody of the invention by simple adsorption or optionally after activation of the carrier, for example with glutaraldehyde or cyanogen bromide. Then test solutions containing antibodies directed against HMW-MAA and finally polyclonal antibodies which also react with the anti-HMW-MAA antibodies and which are radioactively labelled, e.g. with $^{125}$I, are added. The amount of antibodies directed against HMW-MAA in the test solution is directly proportional to the amount of bound polyclonal antibodies and is determined by measuring the radioactivity of the solid phase.

The antiidiotypic monoclonal antibodies according to the invention can be used as such or in the form of enzyme-conjugated derivatives in an enzyme immunoassay. As described above for radioimmunoassays, any of the known modifications of an enzyme immunoassay can be used.

The tests are carried out in an analogous manner to the radioimmunoassays described above using an enzyme label instead of a radioactive label. The amount of immune complex formed which corresponds to the amount of antibodies directed against HMW-MAA present in the test solutions is determined by adding an enzyme substrate solution. The enzyme substrate reaction results, for example, in a color change which can be observed by eye or with optical measuring devices.

The antiidiotypic monoclonal antibodies according to the invention can be used as such or in the form of derivatives conjugated with chemiluminescent markers in a chemiluminescence immunoassay. As described above for radioimmunoassays, any of the known modifications of a chemiluminescence immunoassay can be used.

The tests are carried out in an analogous manner to the radioimmunoassays described above using a chemiluminescent label instead of a radioactive label. The amount of immune complex formed which corresponds to the amount of antibodies directed against MW-MAA antigens present in the test solutions is determined by adding a compound triggering luminescence, e.g. $H_2O_2$ and NaOH, and measuring the emission of light with optical measuring devices.

The use according to the invention of antiidiotypic monoclonal antibodies and derivatives thereof as described hereinbefore for the determination of antibodies directed against HMW-MAA antigens also includes other immunoassays known Per se, for example immunofluorescence assays, latex agglutination, hemagglutination, evanescent light assays using an optical fiber coated with an antiidiotypic MAb and other direct-acting immunosensors which convert the binding event into an electrical or optical signal, or the like.

The invention also concerns test kits for the qualitative and quantitative determination of antibodies directed against HMW-MAA comprising antiidiotypic monoclonal antibodies of the invention and/or derivatives thereof and, optionally, other polyclonal or monoclonal antibodies and/or adjuncts.

Test kits according to the invention for a radioimmunoassay contain, for example, a suitable carrier, optionally freeze-dried solutions of one or more polyclonal and/or monoclonal antibodies, solutions of a radioactively labelled antibody, standard solutions of antibodies directed against HMW-MAA antigens, buffer solutions, and, optionally, polypeptides or detergents for preventing non-specific adsorption and aggregate formation, pipettes, reaction vessels, calibration curves, instruction manuals and the like. One of the antibodies of the test kit is an antiidiotypic monoclonal antibody of the invention.

Test kits according to the invention for an enzyme immunoassay contain, for example, a suitable carrier, optionally freeze-dried solutions of one or more polyclonal and/or monoclonal antibodies, optionally freeze-dried or concentrated solutions of an enzyme- or biotin-conjugated antibody, solutions of an enzyme-avidin conjugate if biotin-labelled antibody is used, enzyme substrate in solid or dissolved form, standard solutions of antibodies directed against HMW-MAA, buffer solutions, and, optionally, polypeptides or detergents for preventing non-specific adsorption and aggregate formation, pipettes, reaction vessels, calibration curves, instruction manuals and the like. One of the antibodies of the test kit is a antiidiotypic monoclonal antibody of the invention.

The invention particularly concerns the antibody, the recombinant DNAs, the transformed host cells, the pharmaceutical preparations, and the methods for the preparation thereof as described in the Examples.

The following examples illustrate the invention but do not limit it to any extent.

| Abbreviations | |
|---|---|
| ATP | adenosine triphosphate |
| bp | base pair |
| BSA | bovine serum albumin |
| CDR | complementarity determining region |
| CIAP | calf intestinal alkaline phosphatase |
| CIAP-buffer (10×) | 10 mM $ZnCl_2$, 10 mM $MgCl_2$, 0.5 M Tris-HCl, pH 7.6 |
| DNA ligase buffer (10×) | 0.1 M $MgCl_2$, 0.5 M Tris-HCl, pH 7.6 |
| dNTP | deoxyribonucleotide triphosphate |
| DTT | dithiothreitol |
| EDTA | ethylenediaminetetraacetic acid |
| FCS | fetal calf serum |
| H-chain | heavy chain |
| HEPES | N-2-hydroxyethyl-piperazine-N'-2-ethane-sulfonic acid |
| HMW-MAA | High Molecular Weight-Melanoma Associated Antigen |
| HT | hypoxanthine/thymidine |
| L-chain | light chain |
| Ig | immunoglobulin |
| kb | kilobase pairs |
| MAb | monoclonal antibody(ies) |
| NT-buffer (10×) | 0.1 M $MgCl_2$, 1 mM dithiothreitol, 500 μg BSA/ml (Serva, Fraction V), 0.5 M Tris-HCl, pH 7.5 |
| PBS | phosphate buffered saline solution (Dulbecco & Vogt, J. Exp. Med. 99, 167, 1954) |
| PBS-CM | PBS without $MgCl_2$ and $CaCl_2$ |
| PCR-buffer (10×) | 15 mM $MgCl_2$, 0.5 M KCl, 0.1 M β-mercaptoethanol, 0.5% (w/v) Tween-20 ™ (Merck), 0.5% (w/v) NP-40 ™ (Merck), 0.1 M Tris-HCl, pH 8.3 |
| PNK-buffer | 0.1 M $MgCl_2$, 1 mM EDTA, 0.5 M Tris-HCl, pH 7.5 |
| RIA-buffer | PBS-buffer containing 1% BSA (Serva, Fraction V), 0.2% $NaN_3$ (Merck), 0.05% (w/v) Tween-20 ™ (Merck) |
| RT-buffer (5×) | 15 mM $MgCl_2$, 0.375 M KCl, 50 mM DTT, 0.25 M Tris-HCl, pH 8.3 |
| Substrate buffer | 10% (v/v) diethanolamine (Merck), 0.2% $NaN_3$ (Merck), 0.1% $MgCl_2$, pH adjusted to 9.8 with HCl |
| TAE-buffer | 1 mM EDTA, 0.04 M Tris-acetate |
| TBE-buffer | 89 mM boric acid, 2 mM EDTA, 89 mM Tris-borate |
| TE-buffer | 1 mM EDTA, 10 mM Tris-HCl, pH 8.0 |
| Tris | Tris(hydroxymethyl)aminomethane |
| V-region | variable region |

EXAMPLES

Example 1

Cloning and adaptation of functional Ig H- and L-chain V-region exons of murine hybridoma MK2-23for expression in Sp2/0 myeloma cells General methods used are described in detail in Sambrook et al. (Molecular Cloning: A Laboratory Manual, Second Edition, Cold Spring Harbor Press, 1989).

1.1 Origin of murine hybridoma MK2-23 and preparation of RNA: The manufacture and properties of the murine hybridoma designated MK2-23 is described in the European patent application No. 428 485. It is prepared from B lymphocytes raised in Balb/c mice against idiotypic determinants on the anti-HMW-MAA murine monoclonal antibody 763.74. Total RNA is isolated from ca. $0.5-1\times10^8$ cells using the procedure described by Le Meur et al. (Cell 23, 561–571, 1981).

1.2 In vitro amplification of functional H- and L-chain I-g cDNA sequences: Nucleotide sequences corresponding to the coding regions of Ig genes expressed in the hybridoma MK2-23 are obtained by reverse transcription of total hybridoma RNA, and amplification in vitro of the Ig cDNA transcripts using Taq DNA polymerase. The following oligonucleotide primers are used (letters in brackets signify degenerate nucleotides at these positions):

VH1FOR: 5'-TGAGGAGACGGTGACCGTGGTCCC JTGGCCCCAG-3' SEQ ID No:5
VH1BACK: 5'-AGGT(G/C)(C/A)A(G/A)CTGCAG(G/C) AGTC(T/A)GG-3' SEQ ID No:6
VK1FOR: 5'-GTTAGATCTCCAGCTTGGT(G/C)C(G/C)-3' SEQ ID No:7
VK1BACK: 5'-GACATTCAGCTGACCCAGTCTCCA-3' SEQ ID No:8
M/Cκ: 5'-GGGAAGATGGATACAGTTGG-3' SEQ ID No:9.

M/Cκ corresponds to the reverse antisense strand of the mouse Ig L-chain Cκ constant region exon (Hieter et al., Cell 22, 197–207, 1980). VH1FOR, VH1BACK, VK1FOR and VK1BACK correspond to the Ig H- and L-chain V-region primers described by Orlando et al. (Proc. Natl. Acad. Sci. USA 86, 3833–3837, 1989), with the exception that VK1FOR used here includes two degenerate base substitutions (underlined above). The latter set of primers include DNA restriction sites which facilitate later cloning of amplified V-regions (see example 1.3). These are: VH1FOR: BstEII (GGTGACC SEQ ID No:16); VH1BACK: PstI (CTGCAG SEQ ID No:17); VK1FOR: BglII (AGATCT SEQ ID No:18); VK1BACK: PvuII (CAGCTG SEQ ID No:19).

For reverse transcription and amplification of Ig H-chain mRNA, total MK2-23 hybridoma RNA (10 μg) is treated for 90 min at 37° C. with 200 units of MMLV Reverse Transcriptase (1 μl; Gibco-BRL) in a solution containing 10 μl of RT-buffer, 14 μl of H$_2$O, 2.5 μl of spermidine (10 mM), 0.5 μl of BSA (10 mg/ml), 10 μl of mixed dNTP (2 mM each; N=A, T, G and C), 10 μl of Triton X-100™ (10%, v/v), 1.5 μl of RNAse Block™ (Stratagene) and 1 μl of VH1FOR primer (50 pmol).

A portion (5 μl) of this solution containing Ig cDNA is subjected to in vitro amplification in 100 μl of solution containing:62.5 μl H$_2$O, 10 μl of PCR-buffer, 10 μl of a mixture of dNTP (2 mM each, N=A, T, G and C), 10 ml of dimethyl sulphoxide (Merck) and 2 μl of primers VH1FOR and VH1BACK (50 pmol in H$_2$O). The solution is mixed and heated to 93° C. for 3 min, cooled to 37° C., 0.4 μl of AmpliTaq™ DNA polymerase (Perkin Elmer Cetus) are added, and the solution is overlaid with 100 μl of paraffin oil in a 1 ml Eppendorf™ tube. The solution is then incubated in a temperature cycler (Intelligent Heating Block, Hybaid) as follows:71° C. for 0.2 min, followed by 93° C. for 0.01 min, followed by 37° C. for 0.2 min (4 cycles); 71° C. for 0.2 min, followed by 93° C. for 0.01 min, followed by 62° C. for 0.2 min (30 cycles); 71° C. for 3 min, followed by 62° C. for 0.2 min, followed by 71° C. for 3 min to complete final synthesis of DNA chains. One-tenth volume of the solution is analyzed by electrophoresis on 1% agarose gels containing ethidium bromide in order to visualize amplified DNA products. Successful selective amplification of Ig H-chain sequences results in a DNA band of ca. 350 bp, viewed under u.v. illumination. Occasionally other irrelevent side products of the amplification reaction are observed as DNA bands of different size.

Reverse transcription and in vitro amplification of Ig L-chain mRNA is performed as above for H-chain mRNA, except that for the reverse transcription step the VH1FOR primer is replaced by the M/Cκ oligonucleotide primer, and for the in vitro amplification step the VH1FOR and VH1BACK primers are replaced by VK1FOR and VK1BACK oligonucleotide primers. Successful amplification is monitored as described above for H-chain sequences, using agarose gel electrophoresis, and is indicated by the presence of a ca. 330 bp DNA band under u.v. illumination.

In both cases the amplified material is purified by extraction first with phenol/CHCl$_3$, and then CHCl$_3$. The material is finally precipitated with 2 volumes of ethanol at −20° C. in the presence of 0.3M NaOAc, pH 7.0, washed with 70% ethanol at the same temperature, and the DNA pellet air-dried.

1.3 Cloning of amplified Ig H- and L-chain cDNA sequences: Amplified H- and L-chain cDNA (see example 1.2) is blunt-end cloned after preparing the ends of the DNA fragments by treatment with Klenow DNA polymerase and polynucleotide kinase.

DNA fragments prepared according to example 1.2 are dissolved in TE-buffer (20 μl), added separately to 17 μl of H$_2$O, 5 μl of mixed dNTP (1 mM each, N=A, T, G and C) and 5 μl of NT-buffer, and treated with 15 units (3 μ) of Klenow fragment DNA polymerase I (Boehringer) at room temperature for 30 min. The enzyme is inactivated by heating the solution at 65° C. for 10 min, and the treated DNA samples are electrophoresed using TAE-buffer on 1% agarose gels containing ethidium bromide. DNA bands of ca. 350 bp for amplified H-chain DNA and ca. 330 bp for amplified L-chain DNA, visualised under u.v. illumination, are excised from the gel with a scalpel and purified on separate GENECLEAN™ columns (BIO 101 Inc.) according to the manufacturer's instructions. Each DNA is eluted in 30 μl of manufacturer's elution buffer, to which are added 7.5 μl of H$_2$O.

The purified H- and L-chain cDNA fragments (37.5 μl) are made up separately to 49 μl by the addition of 5 μl of PNK-buffer, 0.5 μl of dithiothreitol, 1 μl of spermidine (50 mM) and 5 μl of ATP (10 mM), and are each treated with 1 μl of T4 polynucleotide kinase (10 units; Pharmacia) at 37° C. for 30 min. The reactions are terminated by the addition of 5 μl of 0.5 mM disodium-EDTA, pH 7.5, followed by 35 μl of TE-buffer and 10 μl of 3M sodium acetate, pH 7.0, after which the DNA solutions are extracted with phenol/CHCl$_3$, CHCl$_3$, and precipitated with 2.5 volumes (v/v) of 95% ethanol. After centrifugation, supernatants are removed and DNA pellets dried and dissolved in 5 μl of TE-buffer.

DNA fragments are cloned in SmaI-digested, dephosphorylated BLUESCRIPT™ KS+ vector (Stratagene). Portions (2 μl) of the polynucleotide kinase-treated H- or L-chain cDNA fragments are separately ligated to 100 ng (1 μl) of prepared BLUESCRIPT™ vector in the presence of 1 μl of DNA ligase buffer, 1 μl of 10×dithiothreitol (0.1M), 0.5 μl of 20×ATP (10 mM), 3.5 μl of H$_2$O, and 1 μl (400 units) of T4 DNA ligase (New England Biolabs.) for 4 h at 14° C.

DNA ligation products are transformed into competent cells of E. coli K12/BZ234 prepared using standard procedures. Ampicillin-resistant clones are picked and plasmid DNA is prepared. Clones with appropriate-sized DNA inserts can be identified by co-digestion of plasmid DNAs with EcoRI+XbaI, which cut the vector polylinker sequence on opposite sides of the SmaI cloning site, and analysing DNA fragments by electrophoresis on 1% agarose gels containing ethidium bromide.

1.4 Identification of functional Ig H- and L-chain gene rearrangements: The nucleotide sequence of cloned plasmids with the correct sized DNA inserts are determined on double-stranded DNA templates with the SEQUENASE™ system using T3 and T7 oligonucleotide primers and the manufacturer's protocol (United States Biochemical). Several plasmid clones with identical sequences are obtained. Sequences of typical clones (MK2-23LPCR1 and MK2-23HPCR1) are listed as SEQ ID NO: 1 and SEQ ID NO: 2 for L- and H-chain, respectively. Sequences shown include the oligonucleotide primers used for the selective in vitro amplification of Ig-related sequences, the position of DNA restriction sites located within the primers, and the location of complementarity-determining regions (CDRs) of the Ig L- and H-chain V-regions, deduced from comparison with the data base of murine Ig V-region sequences (Kabat et al., "Sequences of proteins of immunological interest", fourth edition, U.S. Dept. Health & Human Services, 1987). The predicted N-terminal sequence deduced from MK2-23HPCR1 corresponds to those determined experimentally from N-terminal sequence analysis of the separated H- and L-chains of the mouse MAb MK2-23. In addition to the above, DNA clones are obtained corresponding to a second distinct rearranged Ig L-chain V-region and to an additional, distinct rearranged Ig H-chain V-region. Both of the predicted N-terminal sequences of these additional H- and L-chain rearrangements differ from those of the mouse MAb MK2-23.

The V-region rearrangement of MK2-23LPCR1 uses the J2 L-chain J-minigene joining exon (beginning at nucleotide position 298; SEQ ID NO: 1) and includes a continuous open reading frame encoding a polypeptide sequence formed by V-J exon fusion, characteristic of a functional Ig L-chain gene rearrangement.

The V-region rearrangement of MK2-23HPCR1 uses the $J_H1$ H-chain J-minigene joining exon (beginning at nucleotide position 321; SEQ ID NO:3) and includes a continuous open reading frame encoding a polypeptide sequence formed by V-D-J exon fusion, characteristic of a functional Ig H-chain gene rearrangement.

Apart from the sequences described above, occasional other DNA clones are obtained using MK2-23 cell mRNA, none of which resemble Ig H- or L-chain V-region sequences. The sequences of at least two independent cloned plasmids containing H- and L-chain sequences are compared and shown to be identical, to reduce the possibility that sequences resulting from in vitro amplification contain point mutations in the V-region sequences.

Example 2

Construction of cloning vectors for DNA manipulation 2.1 Vector KS+exPvuII: In order to facilitate cloning MK2-23LPCR1 sequences for expression in BLUESCRIPT™ KS+ plasmid vector (Stratagene), the (two) nonessential PvuII restriction sites are eliminated. BLUESCRIPT™ KS+ plasmid DNA (10 μg) is digested to completion with PvuII to generate two linear DNA fragments of ca. 2300 and 360 bp. The DNA fragments are separated by electrophoresis on 1% agarose gels containing ethidium bromide, and purified using GENECLEAN™ (BIO 101 Inc.). This provides ca. 150 ng of purified 360 bp fragment and ca. 600 ng of 2300 bp fragment. The larger (2300 bp) fragment is treated with 20 units of calf intestinal alkaline phosphatase (CIAP; Boehringer). The CIAP-treated fragments are then extracted with phenol/CHCl$_3$, then CHCl$_3$, precipitated with 0.54 volumes of isopropanol in the presence of 0.3M NaOAc, pH7.0, and the DNA pellet is washed with 70% (v/v) ethanol at −20° C. The pellet is air-dried and dissolved in 6 μl of TE-buffer.

Oligonucleotide linkers (10 ng in 1 μl of H$_2$O) containing an NcoI DNA restriction site (pCCCATGGG; New England Biolabs. SEQ ID No:20) are treated for 30 min at 37° C. with 1 μl of T4 polynucleotide kinase (PL Biochemicals) in a solution containing 36.5 μl of H$_2$O, 5 μl of 10×PNK-buffer, 0.5 μl of 0.1M dithiothreitol, 1 μl of 50 mM spermidine and 5 μl of 10 mM ATP. The phosphorylated linkers are added to 1 μl (150 ng) of the 360 bp PvuII-digested KS+ plasmid DNA fragment and 5 μl of CIAP-treated 2300 bp fragment (200 ng). The mixture of fragments is extracted with phenol/CHCl$_3$, then CHCl$_3$, and precipitated with ethanol in the presence of 0.3M NaOAc, pH 7.0 at −20° C., washed with 70% (v/v) ethanol, air-dried and dissolved in 0.5 ml of H$_2$O. The plasmid DNA/linker mixture is ligated overnight at 4° C. using 10,000 units/5 μl of T4 DNA ligase (New England Biolabs.) in a total volume of 1 ml of solution containing 100 μl of DNA ligase buffer, 100 μl of 0.1M dithiotireitol, 50 μl of 20 mM ATP and 245 μl of H$_2$O. Ligation products are transformed into E. coli K12/BZ234, ampicillin-resistant colonies selected and plasmid DNA preparations made using standard procedures (Sambrook et al., op. cit., Section 1.82–84 & Section 1.25–28). Plasmids having acquired NcoI-linkers ligated at both of the junctions between the 360 bp and 2300 bp DNA fragments are detected by DNA restriction analysis using NcoI.

The NcoI restriction sites are removed from one such plasmid by digesting to termination with NcoI, treating a sample of the digested DNA with Klenow DNA polymerase to generate blunt-end fragments and eliminate the NcoI "sticky-ends", and religation of the fragments using T4 DNA ligase, all using standard procedures as described above and in example 1.3.

The final plasmid, designated KS+ exPvuII, contains NcoI linkers at the original locations of the PvuII restriction sites in the KS+ vector, in which the NcoI restriction sites have been eliminated using Klenow DNA polymerase. The relative orientation of the 360 bp and 2300 bp KS+ DNA fragments and the polylinker DNA cloning sites remain the same as in the BLUESCRIPT™ KS+ vector.

2.2 Vectors KS+ VHX–Vec and KS+ VKX–Vec: The vectors M13-VHPCR1 and M13-VKPCR1 (Orlandi et al., Proc. Natl. Acad. Sci. USA 86, 3833–3837, 1989, made available by The Medical Research Council, 20 Park Crescent, London W1N 4AL) contain 817 bp and 648 bp BamHI/HindIII restriction fragments, respectively, capable of accepting Ig H- and L-chain V-region DNA sequences amplified from MK2-23 cell RNA using oligonucleotides as described in examples 1.2 and 1.3. These BamHI/HindIII vector DNA fragments contain mouse Ig promoters, leader peptide exons and functional rearranged V-D-J and V-J V-region exons.

This DNA is transformed into E. coli K12/TG1, and plasmid DNAs are prepared using standard procedures: Each bacteriophage DNA preparation is digested separately to termination using BamHI+HindIII, and the smaller BamHI/HindIII fragment isolated in each case (817 bp for M13-VHPCR1, and 648 bp for M13-VKPCR1) by electrophoresis on 0.8% agarose gels containing ethidium bromide. DNA bands of the correct size, visualized under u.v. illumination, are excised from the gel and DNA recovered by electroelution from the agarose followed by phenol/CHCl$_3$ extraction and precipitation with isopropanol. DNA pellets are dried and dissolved separately in 10 μl of TE-buffer.

2.2.1 Vector KS+ VHX-Vec: In M13-VHPCR1 the BamHl/HindIII segment contains unique internal DNA restriction sites for enzymes PstI and BstEII, allowing removal of the "irrelevant" Ig H-chain V-region and replacement by a V-region sequence such as that located between PstI and BstEII restriction sites of MK2-23HPCR 1. The exact location of PstI and BstEII sites in the DNA amplification primers VH1FOR and VH1BACK ensure that the H-chain polypeptide-coding sequence is maintained in the correct translational frame with the surrounding DNA sequences, facilitating expression of the V-region protein.

The 817 bp M13-VHPCR1 DNA fragment is cloned after ligation to BLUESCRIPT™ KS+ vector. The vector is prepared for use by digestion with restriction enzymes BamHI+HindIII, followed by extraction with phenol/CHCl$_3$ and CHCl$_3$, ethanol precipitation, centrifugation, washing with 70% ethanol, drying the DNA pellet and dissolving in TE-buffer. Ligation is carried out for 6 h at 14° C. in 15 $\mu$l of solution containing 2 $\mu$l of BamHI+HindIII-treated vector DNA (40 $\mu$g), 2.5 $\mu$l of M13-VHPCR1 DNA fragment (2.5 $\mu$l), 1.5 $\mu$l of 10 mM ATP, 1.5 $\mu$l of 0.1M dithiothreitol, 1.5 $\mu$l of DNA ligase buffer, 4.5 $\mu$l of TE-buffer and 1.5 $\mu$l (600 units) of T4 DNA ligase (New England Biolabs.). Ligation products are transformed into E. coli K12/TG1, ampicillin-resistant colonies selected and plasmid DNAs prepared using standard procedures (Sambrook et al., op. cit, Section 1.82–84 & 1.25–28). A clone is selected containing a recombinant plasmid with a BamHI/HindIII insert DNA fragment of 817 bp, and its sequence confirmed as corresponding to the expected fragment derived from M13-VHPCR1 using the SEQUENASE™ system with T3/T7 oligonucleotide primers, using conditions provided by the manufacturer (United States Biochemical). This plasmid is referred to as KS+ VH-Vec.

KS+ VH-Vec is further modified by the introduction of a second XbaI DNA restriction site in addition to the one originally derived from the BLUESCRIPT™ KS+ polylinker. KS+ VH-Vec DNA is digested to termination with restriction endonuclease HindII, and the fragments are dephosphorylated with calf intestinal alkaline phosphatase using standard procedures (see example 2.1). After treatment the DNA is dissolved in TE-buffer at a concentration of 120 ng/ml. After dissolution, the DNA fragments (0.5 $\mu$l) are added to 1 $\mu$l of XbaI oligonucleotide linkers (pCTCTAGAG, 500 ng/$\mu$l ; New England Biolabs. SEQ ID No:21), 1.5 $\mu$l of 10 mM ATP, 1.5 $\mu$l of 0.1M dithiothreitol, 1.5 $\mu$l of DNA ligase buffer and 7.5 $\mu$l of TE-buffer, and ligated overnight at 14° C. using 1.5 $\mu$l (600 units) of T4 DNA ligase (New England Biolabs.). Following ligation, the mixture is used to transform E. coli K12/TG1, ampicillin-resistant colonies are selected and plasmid DNA preparations made using standard procedures, as described above (Sambrook et al., op. cit., Section 1.82–84 & 1.25–28). Plasmids having acquired the XbaI-linker sequence are detected by digestion using restriction endonuclease XbaI. One plasmid is selected and its nucleotide sequence confirmed as having an additional XbaI-linker sequence incorporated at the original HindII restriction site in the BLUESCRIPT™ KS+ sequence. The plasmid is referred to as SK+VHX-Vec.

2.2.2 Vector KS+ VKX-Vec: In M13-VKPCR1, the BamHI/HindIII segment contains unique internal DNA restriction sites for enzymes PvuII and BclI, allowing removal of the "irrelevant" Ig L-chain V-region and replacement by a V-region sequence such as that located between PvuII and BglII restriction sites of MK2-23LPCR1. The exact location of PvuII and BglII sites in the DNA amplification primers VK1FOR and VK1BACK ensures that the L-chain polypeptide-coding sequence is maintained in the correct translational frame with the surrounding DNA sequences, facilitating expression of the V-region protein. Since the DNA restriction enzyme BclI is sensitive to Dam+ methylation, an appropriate Dam⁻host strain, e.g. E. coli K12/BZ103, K12/E3225 or K12/R832, must be used for growth of phage and plasmids where it is intended, as here, to utilize the BclI restriction site for cloning purposes.

The 648 bp BamHI/HindIII DNA fragment of M13-VKPCR1 is cloned in a similar manner to that of M13-VHPCR1 (example 2.2.1) by ligation to BamHI/HindIII-digested KS+ exPvuII vector (described in example 2.1). After transformation colonies are selected, and one containing a recombinant plasmid with a BamHI/HindIII insert fragment of 648 bp is analyzed and its sequence confirmed as corresponding to the expected fragment derived from M13-VKPCR1 using the SEQUENASE™ system with T3/T7 oligonucleotide primers as described above. This plasmid is referred to as KS+ VK-Vec.

The KS+ VK-Vec vector is further modified by introduction of an XbaI-linker at the HindII restriction site in the BLUESCRIPT™ KS+ polylinker sequence, and its sequence confirmed in a similar manner to that described above for KS+ VHX-Vec (example 2.2.1). Plasmid DNA is transformed into E. coli K12/R832 (Dam⁻) in order to maintain its BclI restriction site in the unmethylated state for cloning purposes. The final plasmid vector is referred to as KS+ VKX-Vec.

Example 3

Construction of a vector for Ig H-chain gene expression in myeloma cells 3.1 Isolation of a DNA fragment encoding a human $\gamma$1 H-chain: A human DNA library is constructed in the bacteriophage $\lambda$ vector Charon 4a by limited digestion of human fetal liver DNA with restriction endonucleases HaeIII and AluI using published procedures (Lawn et al., Cell 15, 1157, 1978). Approximately $1 \times 10^6$ independent recombinant phages are plated on E. coli K12/803 and screened for the presence of human Ig H-chain DNA sequences using an homologous murine Ig H-chain DNA probe.

A nick-translated $^{32}$P-labelled mouse IgG H-chain DNA probe corresponding to the XbaI/HhaI fragment of the mouse Ig $\gamma$2b gene locus is used to screen recombinant phage as described previously (Takahashi et al., Cell 29, 671–679, 1982). One DNA clone analyzed (#95/4) contains a 7 kb HindIII DNA segment encompassing the human IgG1 constant region exons CH1, hinge region, CH2 and CH3, as determined by restriction mapping and by nucleotide sequence analysis. The portion of clone #95/4 that is sequenced corresponds to the published human IgG1 gene sequence (EMBL data base sequence entry HUMIGCC4) which starts from one of the terminal (HindIII) restriction sites of the 7 kb HindIII segment (Ellison et al., Nucleic Acids Res. 10, 4071–4079, 1982).

The 7 kb HindIII DNA fragment from clone #95/4 containing the human IgG1 constant region exons is subcloned into the HindIII site of dephosphorylated BLUESCRIPT™ KS+ vector and transformed into E. coli K12/TG1. Ampicillin-resistant colonies are picked, plasmid DNAs prepared and those containing the subcloned 7 kb DNA fragment isolated using standard procedures (Sambrook et al., op. cit, Section 1.82–84 & 1.25–28). Plasmid DNA from one clone is identified in which the HindIII site located 5' of the human IgG1 CH1 exon is oriented next to the XbaI DNA restriction site of the polylinker of BLUESCRIPT™ KS+. The plasmid is designated γ1-KS+.

The entire 7 kb DNA insert of γ1-KS+ containing the human IgG1 coding sequences is recovered by electrophoresis on 1% agarose gels containing ethidium bromide after digestion of γ1-KS+ using EcoRI/XbaI which cleaves the KS+ polylinker on both sides of the human DNA insert (neither enzyme cleaves the 7 kb HindIII insert DNA fragment of γl-KS+). The DNA fragment is electroeluted, extracted with phenol/CHCl$_3$, then CHCl$_3$, and recovered by ethanol precipitation/centrifugation using standard procedures. This DNA is referred to as Fragment 1. The DNA is dissolved in TE-buffer and stored at −20° C.

3.2 Cloning of a DNA fragment containing the murine Ig H-chain transcriptional enhancer: A 686 bp XbaI/EcoRI DNA fragment corresponding to nucleotides 2877–3563 of the murine Ig H-chain gene locus (GENBANK data base entry MUSSIGCD07) containing the murine Ig H-chain transcriptional enhancer is cloned in EcoRI/XbaI-digested BLUESCRIPT™ KS+ vector and its sequence verified using the SEQUENASE™ system with T3 and T7 olignonucleotide primers. The plasmid is designated pDA24/3. The insert DNA fragment of pDA24/3 is isolated after digestion with EcoRI/XbaI, and recovered after electrophoresis on 1% agarose gels containing ethidium bromide using the same procedure used for Fragment 1. The DNA is dissolved in TE-buffer and stored at −20° C. This DNA is referred to as Fragment 2.

3.3 Assembly of plasmid vector Huγ1-EH-gpt: DNA Fragment 1 and Fragment 2 (examples 3.1 and 3.2) are cloned by coligation into vector pSV2gpt (Southern & Berg, J. Mol. App. Genet. 1, 327, 1982), linearised by digestion using EcoR1. The DNA ligation mixture contains digested pSV2gpt vector DNA (50 ng in 1 μl of TE-buffer), Fragment 1 (70 ng in 1.3 μl of TE-buffer), Fragment 2 (7 ng in 1.0 μl of TE-buffer), 1.5 μl of 10 mM ATP, 1.5 μl of 0.1M dithiothreitol, 1.5 μl of DNA ligase buffer, 5.7 μl of TE-buffer and 1.5 μl of T4 DNA ligase (600 units; New England Biolabs.). Ligation is performed overnight at 14° C. After transformation into E. coli K12/TG1, ampicillinresistant recombinants are identified and plasmid DNAs prepared using standard procedures (Sambrook et al., op. cit., Section 1.82–84 & 1.25–28). DNA clones are selected based on the results of restriction analysis using the enzymes EcoRI, BamHI, HindIII, PvuII and XbaI. A plasmid with the appropriate DNA restriction properties is selected and designated Huγ1-EH-gpt. The plasmid contains pSV2gpt sequences and the mouse Ig H-chain enhancer and human IgG1 constant region exons separated by a unique XbaI cleavage site.

Example 4

Construction of a vector for Ig L-chain gene expression in myeloma cells 4.1 Isolation of a DNA fragment encoding the human Cκ L-chain constant region exon: A nick-translated $^{32}$P-labelled murine Ig germline L-chain J-region genomic DNA probe is prepared, corresponding to a ca. 2240 bp HindIII/XbaI segment of Balb/c mouse liver DNA (nucleotide positions 659–2900 of the published germline Ig L-chain locus; Max et al., Proc. Nadl. Acad. Sci. USA 76, 3450–3454, 1979; EMBL data base sequence entry MUSIGKJC2). The probe is used to screen a human recombinant λ phage DNA library for segments containing homologous human Cκ L-chain DNA sequences, using a similar procedure to that described for Ig H-chain sequences (example 3. 1). A positively-hybridizing recombinant phage is selected and DNA prepared using standard procedures.

A DNA fragment is subcloned from the cross-hybridizing recombinant phage, corresponding to a ca. 2.5 kb BalI/EcoRI fragment containing the human Ig Cκ constant region exon (Hieter et al., Cell 22, 197–207, 1980). The BalI DNA restriction site and Cκ coding region are indicated in the EMBL data base sequence entry HUMIGKC3; BalI DNA cleavage site=nucleotide position 31; Cκ coding region= nucleotide position 334–656. The cloning vector used is SmaI/EcoRI-digested BLUESCRIPT ™ KS+, and the methods used are standard cloning procedures (Sambrook et al., op. cit, Section 1.63–70). A recombinant plasmid with the desired DNA restriction characteristics is selected, and its structure confirmed by partially sequencing using the SEQUENASE™ system with T3 and T7 oligonucleotide primers according to the manufacturer's protocol. The plasmid is designated pDA27.

pDA27 contains two DNA restriction sites for the enzyme XbaI; one derived from the KS+ polylinker, the second being a site in the human Cκ DNA insert of pDA27 located ca. 1 kb from the EcoRI site. In order to facilitate subsequent use in the construction of expression vectors the latter DNA restriction site is eliminated as follows: pDA27 DNA (30 μg) is partially digested with 4 μl of XbaI (1 unit/μl ; Boehringer) for 45 min at 37° C. The DNA is then extracted with phenol/CHCl$_3$, CHCl$_3$, ethanol precipitated and dissolved in 82 μl of distilled H$_2$O to which is added 10 μl of NT-buffer, 4 μl of mixed dNTPs (2 mM each; N=A, T, G and C). Klenow fragment DNA polymerase (4 μl ; 4.9 units/μl ; Boehringer) is added and the mixture incubated at room temperature for 30 min, after which the enzyme is heat-inactivated by heating at 65° C. for 5 min. Partial digestion generates DNA fragments of ca. 5.5 kb which are separated from terminal digestion products by electrophoresis on a 0.8% agarose gel containing ethidium bromide. After electrophoresis the 5.5 kb DNA band is electroeluted from the agarose gel and recovered by phenol/chloroform extraction and ethanol precipitation as described above. The DNA pellet is dissolved in 20 μl of TE-buffer (yield approx. 40 ng). One-half of the material is religated, transformed into E. coli K12/BZ234, and ampicillin-resistant colonies are selected. Plasmid DNA is prepared from appropriate clones and digested with a combination of EcoRI+XbaI. Plasmids with the correct XbaI site eliminated generate two EcoRI/XbaI DNA restriction fragments; one of ca. 3 kb (containing KS+ vector sequences) and one of 2.5 kb (human Cκ-containing fragment). One such plasmid is selected and referred to as pDA28.

The 2.5 kb human DNA fragment of pDA28, now containing an XbaI DNA restriction site (derived from the KS+ polylinker) located 5' of the human Cκ-coding region, is recovered from the plasmid by digestion with EcoRI/XbaI, and purified by electrophoresis on 0.8% agarose gels followed by extraction with phenol/CHCl$_3$, then CHCl$_3$, ethanol precipitation, drying and dissolution in TE-buffer. The DNA is referred to as Fragment 3.

4.2 Assembly of plasmid vector HuCκ-EH-neo: DNA Fragment 2 (ca. 700 bp EcoRI/XbaI DNA fragment containing the murine Ig H-chain transcriptional enhancer; example 3.2) and Fragment 3 (ca. 2.5 kb EcoRI/XbaI DNA fragment containing the human Cκ coding region; example 4.1) are cloned by coligation into vector pSV2neo (Southern & Berg, J. Mol. App. Genet. 1, 327, 1982), linearized by digestion using EcoRI. DNA is ligated overnight at 14° C. in a mixture containing 20 ng of EcoRI-digested pSV2neo DNA (1 μl), 15 ng of DNA Fragment 2 (1 μl), 25 ng of DNA Fragment 3 (0.5 μl), 2 μl of DNA ligase buffer, 2 μl of 10 mM ATP, 2 μl of 0.1M dithiothreitol and 10 μl of H$_2$O, using 1 μl of T4 DNA ligase (400 units/μl ; New England Biolabs.). The ligation mixture is transformed into *E. coli* K12/803, ampicillin-resistant colonies are selected, and plasmid DNAs prepared using standard procedures (Sambrook et al., op. cit., Section 1.82–84 & 1.25–28). Plasmids are analyzed by digestion with EcoRI/XbaI and PstI, and one with the desired orientation of DNA fragments selected, referred to as HuCκ-EH-neo.

Example 5

Vectors for expression of chimeric mouse/human antiidiotypic monoclonal antibody in myeloma cells 5.1 Generation of the chimeric Ig H-chain expression vector MK2-23-Huγ1: Vector KS+ VHX–Vec (7.5 μg; example 2.2.1) is digested to termination using restriction endonucleases BstEII/XbaI, and the DNA fragments fractionated on a 0.8% agarose gel containing ethidium bromide. Digestion releases the "irrelevant" V-region gene segment (ca. 330 bp) and a ca. 3.3 kb BstEII/XbaI vector DNA fragment, which is excised from the gel, recovered by electroelution, extracted with phenol/CHCl$_3$, then CHCl$_3$, and precipitated with ethanol. The DNA pellet obtained after centrifugation is washed in 70% ethanol at −20° C. and dissolved in distilled H$_2$O. Plasmid MK2-23HPCR 1 (ca. 30 μg; example 1.4) is digested to completion with restriction endonucleases BstEII/PstI, releasing a ca. 330 bp DNA fragment containing the cloned MK2-23 Ig H-chain V-region (SEQ ID NO:3). The fragment is separated from vector sequences by electrophoresis on a 1% agarose gel, recovered by fractionation using GENECLEAN™ (BIO 101 Inc.) using the procedure provided by the manufacturer. DNA is precipitated at −20° C. with 2.5 volumes of 95% ethanol in the presence of 0.3M NaOAc, pH 7.0, washed using 70% ethanol at the same temperature, and dissolved in TE-buffer. The yield is ca. 600 ng of DNA.

The isolated ca. 3.3 kb vector DNA fragment (100 ng in 2 μl of H$_2$O) isolated from KS+ VHX–Vec as described above is ligated overnight at 4° C. together with the isolated ca. 330 bp MK2-23 Ig H-chain V-region DNA fragment (10 ng in 1 μl of TE-buffer) in the presence of 1 μl of DNA ligase buffer, 1 μl of 0.1M dithiothreitol, 0.5 μl of 20 mM ATP, 3.5 μl of H$_2$O and 1 μl of T4 DNA ligase (400 units/μl; New England Biolabs.). DNA ligation products are transformed into *E. coli* K12/BZ234, ampicillin-resistant colonies selected, and plasmid DNA clones identified. Several clones are identified with the expected DNA restriction properties, and one clone containing the MK2-23 Ig H-chain V-region sequenced using the SEQUENASE™ system with T3/T7 oligonucleotide primer, using the manufacturer's protocol. The DNA clone is referred to as clone #782.

Clone #407 contains the MK2-23 Ig H-chain V-region adapted for expression by incorporation into the M13-VHPCR1 cassette (described in example 2.2). The adapted H-chain V-region exon, plus the H-chain leader peptide exon and promoter element derived from the M13-VHPCR1 cassette, are released together from clone #407 on a ca. 830 bp DNA fragment by digestion with XbaI. The XbaI fragment is separated from the larger vector-containing DNA fragment by electrophoresis on a 0.8% agarose gel, purified by phenol/CHCl$_3$ extraction and ethanol precipitation by standard procedures, and dissolved in TE-buffer. The DNA fragment is ligated to plasmid vector Huγ1-EH-gpt (example 3.3) as follows: 200 ng of XbaI-digested, dephosphorylated Huγ1-EH-gpt (in 2 1μl of TE-buffer) and 10 ng of isolated DNA fragment (in 0.5 μl of TE-buffer) are added to 2 μl of DNA ligase buffer, 2 μl of 0.1M dithiothreitol, 1 μl of 20 mM ATP and 10.5 μl of H$_2$O. DNA ligation is performed overnight at 4° C. using 2 μl of T4 DNA ligase (800 units; New England Biolabs.). DNA ligation products are transformed into *E. coli* K12/BZ234, ampicillin-resistant colonies selected and plasmid DNAs prepared using standard procedures (Sambrook et al., op. cit, Section 1.82–84 & 1.25–28). Plasmids containing the inserted ca. 830 bp XbaI DNA fragment in the required orientation for expression are detected by using BstEII. Plasmid DNA is prepared from one DNA clone, referred to as MK2-23-Huγ1H3.

5.2 Generation of the chimeric Ig L-chain expression vector MK2-23-HuCκ: Vector KS+ VKX–Vec (60 μg; example 2.2.2) is digested to termination using restriction endonucleases BclI/PvuII, dephosphorylated by treatment with calf intestinal alkaline phosphatase using a standard procedure (see example 2.1) and the DNA fragments fractionated on a 0.8% agarose gel containing ethidium bromide using TBE-buffer. Digestion releases the "irrelevant" V-region gene segment (ca. 300 bp) and a ca. 3.3 kb BclI/PvuII vector DNA fragment, which is excised from the gel, recovered by electroelution, extracted with phenol/CHCl$_3$, then CHCl$_3$, and precipitated with isopropanol. The DNA pellet obtained by centrifugation is washed in 70% ethanol at −20° C. and dissolved in 100 μl of TE-buffer.

Plasmid MK2-23LPCR1 (example 1.4) is digested to completion with restriction endonucleases BglII/PvuII, releasing a ca. 380 bp DNA fragment containing the cloned MK2-23 Ig L-chain V-region (SEQ ID NO:1). The fragment is separated from vector sequences by electrophoresis on a 0.8% agarose gel, recovered by electroelution, extracted with phenol/CHCl$_3$, then CHCl$_3$, precipitated at −20° C. with 2.5 volumes of 95% ethanol in the presence of 0.3M NaOAc, pH 7.0, washed using 70% ethanol at the same temperature, and dissolved in TE-buffer.

The ca. 3.3 kb dephosphorylated vector DNA fragment (200 ng in 2 μl TE-buffer), isolated from KS+ VKX–Vec as described above, is ligated together with the isolated ca. 320 bp MK2-23 Ig L-chain V-region DNA fragment (50 ng in 1 μl of TE-buffer) in the presence of 2 μl of 0.1M dithiothreitol, 1 μl of 20 mM ATP, 10 μl of H$_2$O, 2 μl of DNA ligase buffer and 2 μl (800 units; New England Biolabs.) of T4 DNA ligase. DNA ligation products are transformed into *E. coli* K12/BZ234, ampicillin-resistant colonies selected, plasmid DNA isolated and clones identified by restriction analysis using XbaI, and sequence analysis performed using the SEQUENASE™ system with T3 and T7 oligonucleotide primers according to the manufacturer's protocol. One clone is selected. The DNA clone is referred to as clone #1401.

Clone #1401 contains the MK2-23 Ig L-chain V-region adapted for expression by incorporation into the M13-VKPCR1 cassette (described in example 2.2). The adapted L-chain V-region exon, plus the L-chain leader peptide exon and promoter element derived from the M13-VKPCR1 cassette, are released together from clone #1401 on a ca. 650 bp DNA fragment by digestion with XbaI. This smaller XbaI DNA fragment is separated from the larger vector-containing DNA fragment by electrophoresis on a 0.8% agarose gel, purified by phenol/CHCl$_3$ extraction and ethanol precipitation by standard procedures, and dissolved in TE-buffer. The DNA fragment is ligated to plasmid vector HuCκ-EH-neo (example 4.2) as follows: 100 ng of XbaI-digested, dephosphorylated HuCκ-EH-neo (in 1 μl of TE-buffer) and 20 ng of isolated DNA fragment (in 4 μl of TE-buffer) are added to 1 μl of DNA ligase buffer, 1 μl of 0.1M dithiothreitol, 0.5 µl of 20 mM ATP, 1.5 µl of H$_2$O, and 1 µl of T4 DNA ligase (400 units; New England Biolabs.). Ligation is performed for 2 h at 15° C. DNA ligation products are transformed into *E. coli* K12/BZ234, ampicillin-resistant colonies selected and plasmid DNAs prepared using standard procedures (Sambrook et al., op. cit, Section 1.82–84 & 1.25–28). Plasmids containing the inserted ca. 650 bp XbaI DNA fragment in the required orientation for expression are detected by digestion using restriction endonuclease PstI. DNA from one such plasmid is prepared, and is referred to as MK2-23-HuCκ1406.

Example 6

Transfection of Sp2/O myeloma cells using MK2-23-Huγ1H3 and MK2-23-HuCκ1406

6.1 Growth and preparation of cells: Sp2/0 (ATCC CRL 1581) is a well-characterized mouse cell-line of lymphoid origin. It is an Ig non-secreting variant of a cell-line obtained from the fusion of a mouse spleen cell with the myeloma X63-Ag8, a subline of the myeloma MOPC-21 (Köhler and Milstein, Eur. J. Immunol. 6, 511, 1976; Shulman et al., Nature 276, 270, 1978). Sp2/0 cells are grown at 37° C. in HB101™ medium (Hana Biologics), supplemented with 5% (v/v) FCS (Amimed), 1 mM sodium pyruvate (Gibco), 2 mM L-glutamine (Amimed), 10 mM HEPES buffer, pH 7.4 (Serva) and 10 µg/ml gentamycin (Sigma).

Cells are grown in a humidified atmosphere of air and 5% CO$_2$ in a tissue culture incubator (Brouwer, model 3035) in 175 cm$^3$ tissue culture flasks (Costar, 3151). Cells are harvested by gentle centrifugation in 50 ml sterile tubes (Falcon 2070) at 4° C. (200×g, 800 rev/min; Beckman J-6B/P centrifuge), frozen and stored at -120° C. in HB101™ (Hana Biologics) containing 15% FCS (Amimed) and 7.5% (v/v) dimethyl sulphoxide (Serva) in clean, sterile plastic capped tubes. 24 h before transfection, Sp2/0 cells are passaged into fresh growth medium at a concentration of 1×10$^5$ cells/ml. Immediately before transfection, cells are harvested as described above, and the cell pellets (total no. of cells ca. 9×10$^7$) washed twice in PBS-CM at 4° C. and resuspended in the same buffer at a concentration of ca. 1×10$^8$ cells/ml.

6.2 Preparation of DNA fragments and transfection: For transfection, plasmid DNAs MK2-23-Huγ1H3 (example 5.1) and MK2-23-HuCκ1406 (example 5.2) are digested to termination using restriction endonuclease EcoRI to release the chimeric mouse:human Ig H- and L-chain insert DNA fragments. Digested DNA is extracted with phenol/CHCl$_3$, then CHCl$_3$, precipitated at –20° C. with ethanol in the presence of 0.3M NaOAc, pH 7.0, washed with 70% ethanol at the same temperature, and resuspended in TE-buffer.

Samples (5 µg) of each digested plasmid DNA are combined (total volume of 15 µl in TE-buffer) and added to 2×10$^7$ (200 µl) of Sp2/0 cells at 0° C., previously grown, washed and resuspended in PBS-CM as described above (example 6.1). The cells plus DNA are drawn into the barrel of a TA750 electrotransfection apparatus (Kruess GmbH), pre-cooled to 0° C. using ice-cold sterile PBS-CM. Cells are subjected to two electrical pulses of 3500 V/cm for 10 µs, with a 30 s interval between pulses, using the cylindrical electroporation chamber provided by the manufacturer. Cells are expelled gently into a clean, sterile cryotube (Nunc) and kept on ice for 10 min, after which they are diluted (1:3, v/v) into supplemented HB101™ growth medium (see above, example 6) containing 15% (v/v) FCS (Amimed) and incubated at room temperature for 20 min. The cells are then further diluted to 100 ml in the same growth medium and 1 ml samples distributed into wells of 24-well Nunclon™ tissue culture clusters (Delta). After incubation for 24 h at 37° C., as described above, 0.5 ml of the growth medium in each well are removed and replaced with 0.5 ml of prewarmed selection medium containing supplemented HB101™ (Hana Biologics)+15% (v/v) FCS (Amimed) supplemented with a 1:45 dilution of HT (Sigma, 50×HT media supplement) and 1 mg/ml geneticin (Gibco). One-half (0.5 ml) of the medium is replaced every 48 h with additional selection medium, as described above, and selection continued for at least 14 days.

Example 7

Identification of transfectomas secreting chimeric monoclonal antibody

Clones secreting Ig are identified by ELISA using anti-human Ig κ-chain and anti-human IgG antibodies as follows:96-well microtitre plates (Nunclon™ maxisorp) are coated overnight with 50 µl of a 1:500 (v/v) dilution of goat anti-human κ antibody (Tago, 4106) in PBS by incubation at 4° C. Plates are then washed six times with PBS+0.05% Tween-20™ (Fluka), followed by incubation for 20 min at 37° C. with RIA-buffer (100 µl/well). Plates are rewashed six times with PBS+0.05% Tween-20™ (Fluka). Cell-culture supernatants from transfectoma clones (example 6.1) are diluted using RIA-buffer, 50 µl samples added to each well, and the microtitre plates incubated for 2 h at 37° C. Following incubation with cell culture supernatants, plates are washed six times using PBS+0.05% Tween-20™ (Fluka), after which 50 µl/well of alkaline phosphatase-conjugated monoclonal mouse anti-human γ heavy chain antibody in RIA-buffer (1:1000, v/v dilution; Sigma A-1668) are added and the plates incubated 2 h at 37° C. Plates are again washed six times with PBS+0.05% Tween-20m (Fluka), and p-nitrophenyl phosphate substrate is added (100 µl/well; Sigma 104 phosphatase substrate tablets; 4×5 mg tablets dissolved in 20 ml of substrate buffer), after which the plates are incubated in the dark for 10 min at room temperature. The plates are blocked by incubation with 0.5M NaOH (100 µl/well) and A$_{405}$ measured using a photometer (TITERTEK™, multiscan MCC). Concentrations of recombinant MAb are determined with reference to a standard consisting of dilutions of a purified mouse:human chimeric antibody of identical human isotype (IgG1,κ).

Cells from positive wells are cloned by limited dilution. One cell-line designated MK2-CHγ1-6 which produces recombinant MAb MK2-CHγ1 is selected.

Example 8

Specificity of the mouse/human chimeric MAb MK2-CHγ1 a) ELISA

The murine anti-idiotypic MAb MK2-23 recognizes idiotypic determinants on the murine MAb 763.74 (see example 1), a monoclonal antibody of IgG1, κ isotype.

Microtitre plates (96-well Nunclon™ maxisorp) are coated overnight with 50 µl of a 1:85 (v/v) dilution of purified murine MAb 763.74; stock concentration 0.85 mg/ml) in PBS, by incubation at 4° C. Plates are then washed six times with PBS+0.05% Tween-20™ (Fluka), followed by incubation for 20 min at 37° C. with RIA-buffer (100 µl/well). Plates are rewashed six times with PBS+ 0.05% Tween-20™ (Fluka). Cell culture supernatants from the transfectoma MK2-CHγ1-6 and two isotype-matched (IgG1, κ) chimeric antibodies of different, distinct specificities (CHCl-13-33 and F5-CHγ1) as negative control are diluted separately using RIA-buffer, 50 μl added to microtitre wells, and the plates incubated for 2 h at 37° C. Following incubation, plates are washed six times using PBS+0.05% Tween-20™ (Fluka), after which 50 μl/well of conjugated antibodies are added. The antibody conjugate is alkaline-phosphatase conjugated monoclonal mouse anti-human γ heavy chain (1:1000, v/v dilution; Sigma A 1668). Plates are then incubated for 2 h at 37° C. Plates are again washed six times with PBS+0.05% Tween-20™ (Fluka), and p-nitrophenyl phosphate substrate is added (100 μl/well; Sigma 104 phosphatase substrate tablets; 4×5 mg tablets dissolved in 20 ml of substrate buffer), after which plates are incubated in the dark for 10 min at room temperature. The plates are blocked by incubation with 0.5M NaOH (100 μl/well), and $A_{405}$ is measured using a photometer (TITERTEK™, multiscan MCC). Results ($A_{405}$values) are shown in the following table:

| Developing Antibody (Supernatant) | F5-CHγ1 | CHC1-13-33 | MK2-CHγ1 |
|---|---|---|---|
| anti-human γ | 0.017 | 0.013 | 0.780 | b) Ouchterlony double diffusion assay

Ouchterlony double diffusion assays were done using 5 μl of purified Mab 763.74, MAb MK 2.23 or MAb MK2-CHγ1 (0.5 mg/ml), goat anti-human IgG (Fc) (Jackson 109-005-089) and goat anti-mouse IgG (Fc) (Jackson 115-005-071). Mab MK2-CHγ1 formed precipitation lines only with MAb 763.74, anti-human IgG (Fc) and anti-human K antisera.

|  | MAb 764.64 | anti-human IgG (Fc) | anti-human K | anti-mouse IgG (Fc) |
|---|---|---|---|---|
| MK2-CHγ1 | + | + | + | − |
| MK2-23 | + | − | − | + |
| polyclonal mouse IgG | − | − | − | + |
| polyclonal human IgG | − | + | + | − |

Example 9

Large scale cultivation of transfectoma MK-CHγ1-6

The following growth media are used for large scale cell cultivation: Medium 1 is a 1:1:1 (v/v) mixture of DMEM containing 4.5 g/l D-glucose (Gibco), Nutrient Mix F12 HAM (Gibco) and RPMI 1640 (Gibco) with the following additions: L-glutamine (300 mg/l, Sigma), sodium pyruvate (73 mg/I, Gibco), glucose (1.7 g/l, Fluka), β-mercaptoethanol (2.3 mg/l, Sigma), ethanolamine (13.3 mg/l, Sigma), $NaHCO_3$ (2.3 g/l, Merck), and gentamycin (10 mg/l, Sigma). Medium 2 has the same composition as Medium 1, but further contains 2% (v/v) Ultroser™ HY (Gibco).

Cells of the transfectoma MK-CHγ1-6 (example 7) are adapted to growth under serum-free conditions in Medium 2. Permanent stocks of serum-free adapted cells are stored frozen. For cultivation, cells are passaged in Medium 2 at an initial cell concentration of $4 \times 10^4$ cells/ml at 37° C., 5% $CO_2$, 95% humidity in a Brouwer incubator type 3035. $5 \times 10^8$ cells (91% viability, measured using Trypan Blue™ staining) in 50 ml are used to inoculate an Acusyt-Jr™ automated hollow-fiber cell culture system (Endotronics Inc., Coon Rapids, Tenn. 55433, USA). The culture system is operated according to the manufacturer's instructions using Medium 1 as circulation medium and Medium 2 as cell growth medium. After 7 days growth at 37° C. the cycling of Medium 1 is initiated and the first harvest of culture supernatant taken. Cell cultivation is continued for up to 70 days under normal running conditions. The concentration of the antibody in the cell culture supernatant is determined using the ELISA of example 7.

Example 10

Purification of the chimeric MAb MK2-CHγ1

1000 ml of cell culture supernatant kept at −70° C. are thawed to room temperature and filtered under sterile conditions through a 0.22 μm filter. The filtrate is pumped at 3 ml/min over a column (2.5 cm×4 cm) of Sepharose™ CL-4B (Pharmacia) in order to remove any large aggregated material from the solution. The liquid emerging from this column is directly passed through a second column (2.5 cm×7 cm) of Protein-A agarose (IPA 300, immobilized recombinant Protein-A, Repligen, Cambridge, USA). 100 mM sodium citrate, pH 6.0, is passed through both columns at 3 ml/min until the absorbance at 280 nm (UV-1 monitor, Pharmacia) of the eluate reaches zero and the pH is 6.0 (type 2195 pH/conductivity meter, LKB). The desired antibody bound to the protein-A column is then eluted by pumping 100 mM sodium citrate, pH 4.0, over both columns at 3 ml/min. The eluted antibody is detected by adsorbance at 280 nm and manually collected into sterile 50 ml plastic tubes (Costar). A total volume of 120 ml is collected.

The pooled Protein-A eluate is diluted with sterile water until the conductivity (model 4070 conductivity meter, Jenway, Essex, UK) is reduced to 2.3 mS (total volume 500 ml). This solution is passed at 5 ml/min over a pre-packed column of S-Sepharose™ HP (HR 35/100, Pharmacia) equilibrated in 50 mM sodium acetate, pH 5.0. The column is washed with 50 mM sodium acetate at 5 ml/min until the conductivity and pH reach the original equilibrium value and the UV absorbance reaches zero. The bound antibody is eluted by a gradient of 100% 50 mM sodium acetate, pH 5.0, to 100% 50 mM sodium acetate and 500 mM NaCl, pH 5.0, over 85 min at a flow rate of 3 ml/min. The antibody elutes starting at 53 min in a major peak and a minor peak. Both peaks are manually collected into two sterile plastic 300 ml bottles, the pH adjusted to pH 7.0 with 1M Tris base, and the solutions sterile filtered under aseptic conditions through a 0.22 μm filter (Sterivex-GS™, Millipore) and stored at 4° C. Both the major and the minor peak contain the desired antibody. The difference in mobility on S-Sepharose™ appears to be the result of differences in the antibody glycosylation.

The eluate containing the major peak of protein is reduced to a volume of 20 ml by microfiltration using an Amicon 8050 stirred cell with a YM10 microfiltration membrane. The 20 ml sample of antibody is then loaded automatically onto a S300 HR gel filtration column (1.3×65 cm, Pharmacia) equilibrated in PBS. The eluted antibody is detected by UV absorbance at 280 nm. The protein is collected manually and sterile filtered through a 0.22 μm filter (Millipore) into a sterile polysterene flask. The preparation is stored in the dark at 4° C.

Example 11

Pharmaceutical preparation for parenteral application 10 mg chimeric antiidiotypic monoclonal antibody MK-CHγ1 from example 10 are dissolved in 50 ml PBS. The solution is passed through a bacteriological filter, the filtrate divided into 10 equal parts and filled in ampoules under aseptic conditions. The ampoules are preferably stored in the cold, e.g. at 4° C. This pharmaceutical preparation is suitable for injection and is applied as such or in combination with a pharmaceutical preparation containing Alum, a pharmaceutical preparation containing BCG (Bacillus Calmette-Guérin), or a pharmaceutical preparation containing the muramyl peptide MTP-PE.

Deposition data:
The hybridoma cell-line MK2-CHγ1-6has been deposited at the European Collection Of Animal Cell Cultures (ECACC), Porton Down, Salisbury, Wilts SP40JG, United Kingdom, on Mar. 6, 1992 under the accession number 92030642.

We claim:

1. An antiidiotypic humanized monoclonal antibody designated MK2-CHγ1 which is produced by the hybridoma cell line MK2-CHγ1-6 and deposited at the European Collection of Animal Cell Cultures (ECACC) under the accession number 92030642.

2. A method for the treatment of melanoma comprising administration to a mammal in need of such treatment a pharmaceutically effective amount of an antibody according to claim 1.

3. A pharmaceutical composition comprising an antibody according to claim 1 and a pharmaceutically acceptable carrier.

4. Test kit for the qualitative and quantitative determination of antibodies directed against human high molecular weight-melanoma associated antigen (HMW-MAA) comprising an antibody according to claim 1.

* * * * *